US011719455B2

(12) United States Patent
Mou et al.

(10) Patent No.: US 11,719,455 B2
(45) Date of Patent: Aug. 8, 2023

(54) METHOD FOR INTELLIGENTLY PREVENTING AND HANDLING INDOOR AIR POLLUTION

(71) Applicant: MICROJET TECHNOLOGY CO., LTD., Hsinchu (TW)

(72) Inventors: Hao-Jan Mou, Hsinchu (TW); Ching-Sung Lin, Hsinchu (TW); Chin-Chuan Wu, Hsinchu (TW); Yung-Lung Han, Hsinchu (TW); Chi-Feng Huang, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 0 days.

(21) Appl. No.: 17/521,947

(22) Filed: Nov. 9, 2021

(65) Prior Publication Data
US 2022/0196277 A1    Jun. 23, 2022

(30) Foreign Application Priority Data

Dec. 21, 2020 (TW) .................................. 109145357

(51) Int. Cl.
F24F 11/63    (2018.01)
F24F 11/58    (2018.01)
(Continued)

(52) U.S. Cl.
CPC ............ F24F 11/63 (2018.01); F24F 8/10 (2021.01); F24F 11/58 (2018.01); G01N 15/06 (2013.01);
(Continued)

(58) Field of Classification Search
CPC .... F24F 11/63; F24F 8/10; F24F 11/58; F24F 2110/52; F24F 2110/65; F24F 2110/64;
(Continued)

(56) References Cited

U.S. PATENT DOCUMENTS

2017/0130981 A1    5/2017  Willette et al.
2017/0350611 A1*  12/2017  Su .............................. F24F 8/80
2020/0292438 A1    9/2020  Mou et al.

FOREIGN PATENT DOCUMENTS

CN    106996622 A      8/2017
CN    110857807 A *    3/2020    .............. F24F 11/61
(Continued)

Primary Examiner — Alicia M. Choi
(74) Attorney, Agent, or Firm — McClure, Qualey & Rodack, LLP

(57) ABSTRACT

A method for intelligently preventing and handling indoor air pollution is adapted to be implemented in an indoor space and includes providing a cloud processing device to receive and intelligently compare an outdoor gas detection data, an indoor gas detection data, and device gas detection data with each other. Then, the cloud processing device remotely transmits a control signal to the communication relay station and further to an indoor gas exchange system, so that the indoor gas exchange system is capable of intelligently enabling the gas processing device and controlling the operation time of the gas processing device for exchanging a polluted gas in the indoor space with the outdoor gas. Moreover, the gas exchanger can perform purification for the polluted gas at the location of the gas exchanger, thereby allowing the polluted gas in the indoor space to be exchanged into a clean, safe, and breathable gas.

33 Claims, 18 Drawing Sheets

(51) Int. Cl.
*F24F 8/10* (2021.01)
*G01N 15/06* (2006.01)
*G01N 33/00* (2006.01)
*G05B 17/02* (2006.01)
*F24F 110/52* (2018.01)
*F24F 110/65* (2018.01)

(52) U.S. Cl.
CPC ......... *G01N 33/0009* (2013.01); *G05B 17/02* (2013.01); *F24F 2110/52* (2018.01); *F24F 2110/65* (2018.01); *G01N 2015/0693* (2013.01)

(58) Field of Classification Search
CPC ............... F24F 2110/66; F24F 2110/70; F24F 2110/72; F24F 2110/74; F24F 8/108; F24F 8/22; F24F 8/30; F24F 11/70; F24F 11/30; F24F 11/0001; F24F 3/16; G01N 15/06; G01N 33/0009; G01N 2015/0693; G01N 15/0205; G01N 2015/0046; G01N 2015/0065; G05B 17/02; B01D 53/885; B01D 2255/802; B01D 2257/504; B01D 2257/7027; B01D 2257/708; B01D 2257/91; B01D 2258/06; B01D 2259/4508; B01D 2259/804; B01D 2259/818; B01D 53/007; B01D 53/30; B01D 53/8668; Y02B 30/70

See application file for complete search history.

(56) References Cited

FOREIGN PATENT DOCUMENTS

| | | | | |
|---|---|---|---|---|
| CN | 111527351 A | | 8/2020 | |
| CN | 111811072 A | * | 10/2020 | .............. F24F 11/52 |
| KR | 20080104744 A | * | 12/2008 | .............. B01D 46/42 |
| KR | 101862087 B1 | * | 7/2018 | .............. B01D 46/44 |
| KR | 102321258 B1 | * | 7/2020 | .............. F24F 11/30 |
| KR | 102321258 B1 | * | 11/2021 | .............. F24F 11/00 |
| TW | M561765 U | | 6/2018 | |
| TW | I645136 B | | 12/2018 | |
| TW | I708934 B | | 11/2020 | |

* cited by examiner

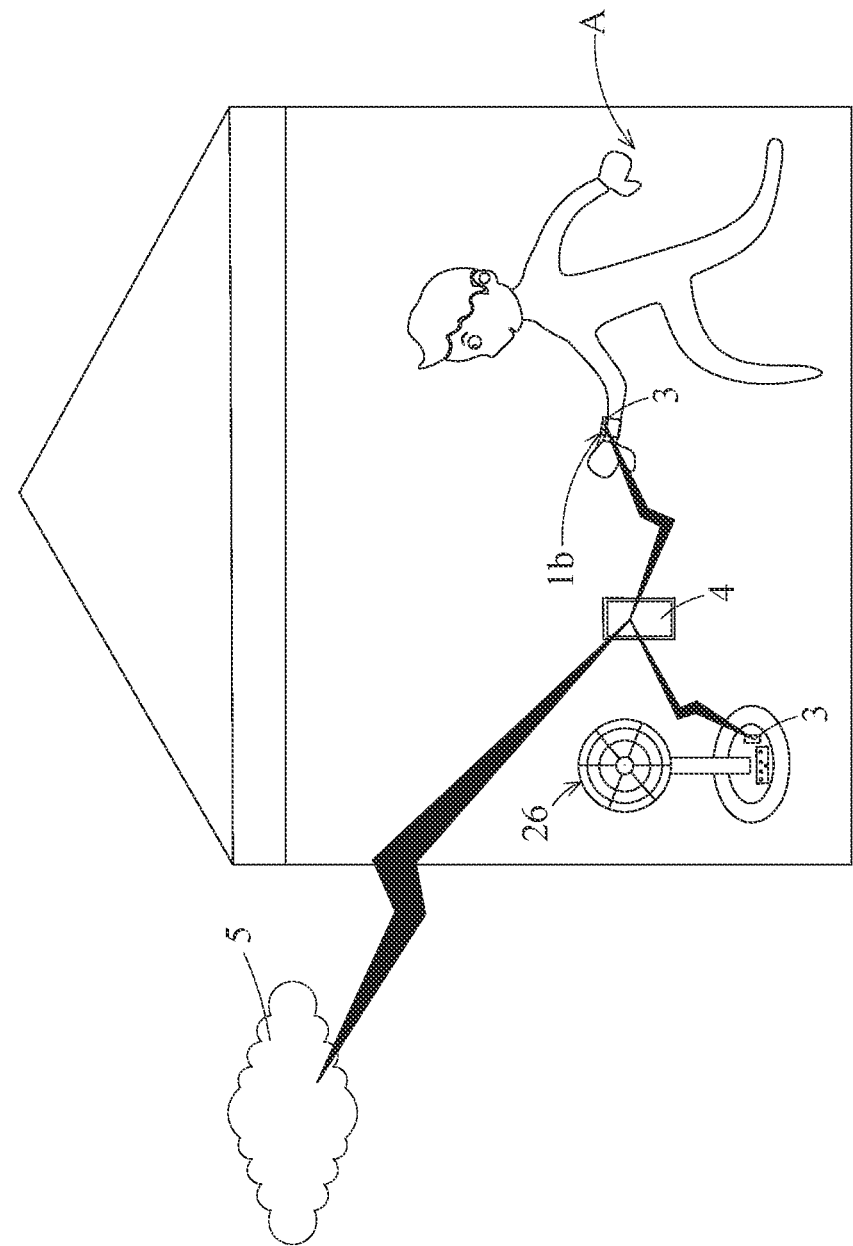

METHOD FOR INTELLIGENTLY PREVENTING AND HANDLING INDOOR AIR POLLUTION

CROSS-REFERENCE TO RELATED APPLICATION

This non-provisional application claims priority under 35 U.S.C. § 119(a) to Patent Application No. 109145357 filed in Taiwan, R.O.C. on Dec. 21, 2020, the entire contents of which are hereby incorporated by reference.

BACKGROUND

Technical Field

The present disclosure relates to a method of performing gas exchange for polluted gas in an indoor space, in particular, to a method for intelligently preventing and handling indoor air pollution.

Related Art

Nowadays people pay more and more attention to the ambient air quality in daily life. It is understood that, gases containing particulate matters (PM1, PM2.5, PM10), carbon dioxide, total volatile organic compounds (TVOC), formaldehyde, etc. or even the particulates, the aerogels, the bacteria, the viruses in the gas might result in adverse effects on the human health, even might be life-threatening when exposure to these gases.

However, since factors affecting the indoor gas quality include not only the gas quality of the outdoor space but also the air conditioning and the pollution source in the indoor space (especially the dusts in the indoor space originated from poor circulation in the indoor space), it is not easy to control the indoor gas quality. In order to improve the indoor gas quality, air conditioners or air cleaners can be utilized. However, the air conditioner and the air cleaner are merely provided for indoor gas circulation and cannot be utilized to eliminate hazardous gases (especially carbon monoxide or carbon dioxide) in the indoor space.

Consequently, it is an issue of this invention to provide a solution that can purify and improve the gas quality of the gas in the indoor space to reduce the risks of breathing hazardous gases and monitor the gas quality of the gas in the indoor space anytime and anywhere to instantly purify the gas quality of the gas in the indoor space.

SUMMARY

One object of the present disclosure is to provide a method for preventing and handling indoor air pollution. In the method, the indoor gas detection data, the outdoor gas detection data, and the device gas detection data are intelligently compared with each other by a cloud processing device, and an indoor gas exchange system intelligently and selectively controls the gas exchange of the gas pollution in the indoor space to the outdoor space, thereby allowing the polluted gas in the indoor space to be exchanged into a clean, safe, and breathable gas. Moreover, the gas exchanger can perform purification for the polluted gas at the location of the gas exchanger, thereby allowing the polluted gas in the location of the gas exchanger to be exchanged into a clean, safe, and breathable gas.

In view of above object, in one embodiment of the present disclosure, a method for intelligently preventing and handling indoor air pollution by filtering and exchanging of a polluted gas in an indoor space is provided. The method includes: detecting a polluted gas in an outdoor space and transmitting an outdoor gas detection data obtained therefrom, wherein an outdoor gas detector is provided to detect the polluted gas in the outdoor space and transmit the polluted gas data in the outdoor space; detecting the polluted gas in the indoor space and transmitting an indoor gas detection data obtained therefrom, where an indoor gas detector is provided to detect the polluted gas in the indoor space and transmit the polluted gas data in the indoor space; providing an indoor gas exchange system in the indoor space for purification so as to detect and transmit a device gas detection data, wherein the indoor gas exchange system comprises at least one gas processing device for a purification of the polluted gas in the indoor space, the at least one gas processing device detects and transmits the device gas detection data of the polluted gas at a location of the at least one gas processing device; and providing a cloud processing device to remotely transmit and intelligently compare the outdoor gas detection data, the indoor gas detection data, and the device gas detection data with each other, wherein the cloud processing device controls the at least one gas processing device to intelligently control the purification by gas exchanging of the polluted gas in the indoor space to the outdoor space; a communication relay station is provided to receive and transmit the outdoor gas detection data, the indoor gas detection data, and the device gas detection data to the cloud processing device for storage and intelligent computation and comparison, thereby the cloud processing device transmits a control command to the communication relay station, and the control command is further transmitted to the at least one gas processing device to intelligently and selectively enable the at least one gas processing device and control an operation time of the at least one gas processing device so as to exchange the polluted gas in the indoor space to the outdoor space and provide the purification of the polluted gas at the location of the at least one gas processing device, thereby allowing the indoor gas detection data of the polluted gas in the indoor space to be decreased to a safety detection value and allowing the polluted gas in the indoor space to be exchanged into a clean, safe, and breathable gas.

BRIEF DESCRIPTION OF THE DRAWINGS

The disclosure will become more fully understood from the detailed description given herein below, for illustration only and thus not limitative of the disclosure, wherein:

FIG. 1E illustrates a schematic view (4) for the operation of the method for preventing and handling indoor air pollution of the exemplary embodiment of the present disclosure;

DETAILED DESCRIPTION

Figure 1A:
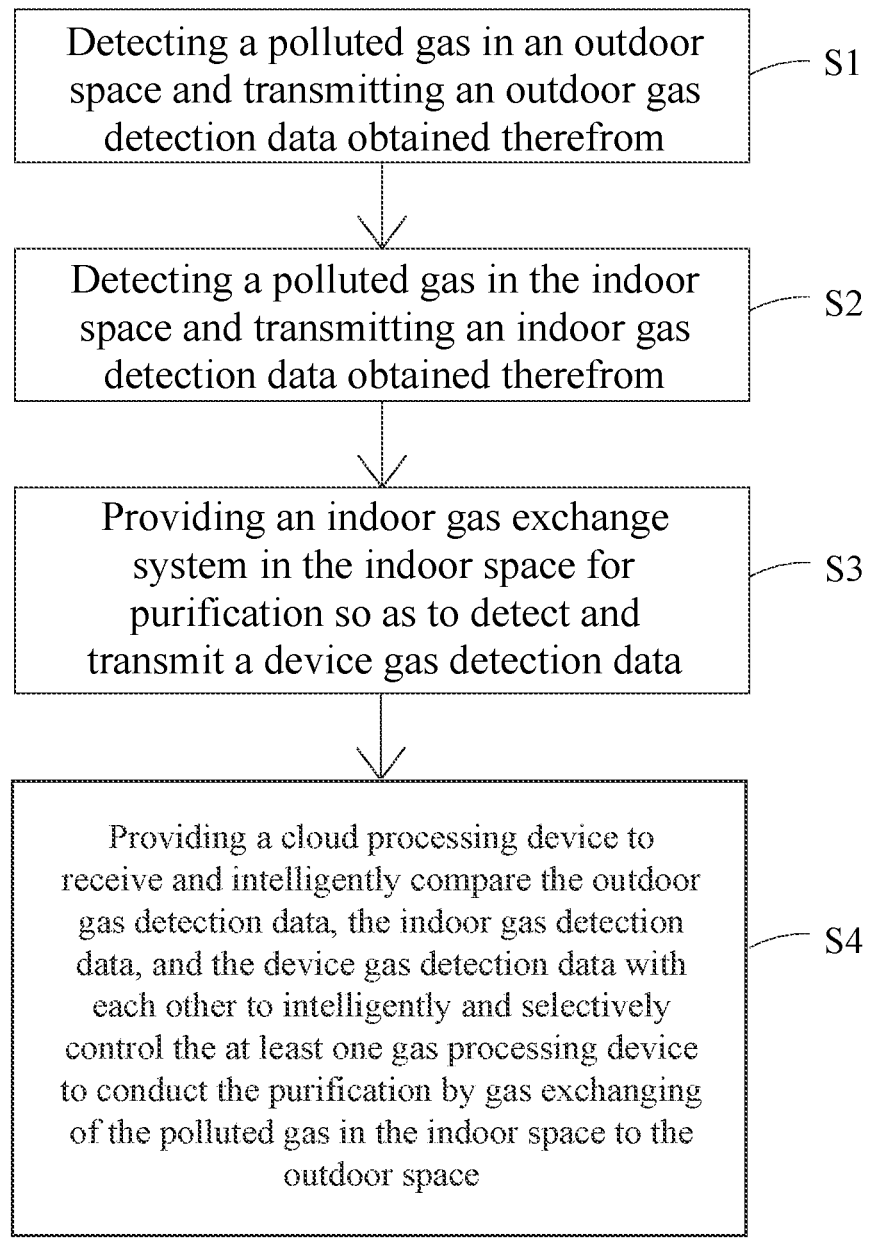
FIG. 1A illustrates a schematic flowchart of a method for preventing and handling indoor air pollution according to an exemplary embodiment of the present disclosure.

The present disclosure will now be described more specifically with reference to the following embodiments. It is to be noted that the following descriptions of different embodiments of this disclosure are presented herein for purpose of illustration and description only, and it is not intended to limit the scope of the present disclosure.

Please refer to FIG. 1A to FIG. 11. A method for intelligently preventing and handling indoor air pollution is provided. This method is applicable for gas filtration and exchange of a polluted gas in an indoor space and includes steps described below.

Firstly, in the step S1, a polluted gas in an outdoor space is detected and an outdoor gas detection data obtained therefrom is transmitted, wherein an outdoor gas detector 1a is provided to detect the polluted gas in the outdoor space and transmit the outdoor gas detection data in the outdoor space.

In the step S2, a polluted gas in an indoor space is detected and an indoor gas detection data obtained therefrom is transmitted, wherein an indoor gas detector 1b is provided to detect the polluted gas in the indoor space A and transmit the indoor gas detection data in the indoor space A.

In the step S3, an indoor gas exchange system 2 is provided in the indoor space A for purification so as to detect and transmit a device gas detection data. The indoor gas exchange system 2 includes at least one gas processing device conducting a purification of the polluted gas in the indoor space A. The gas processing device detects to obtain and transmits the device gas detection data of the polluted gas at a location of the gas processing device.

In the step S4, a cloud processing device 5 is provided to receive and intelligently compare the outdoor gas detection data, the indoor gas detection data, and the device gas detection data with each other, and to remotely transmit data and signals to control the gas processing device, so as to intelligently and selectively control the purification by gas exchanging of the polluted gas in the indoor space to the outdoor space. A communication relay station 4 is provided to receive and transmit the outdoor gas detection data, the indoor gas detection data, and the device gas detection data to the cloud processing device 5 for storage and intelligent computation and comparison, so that the cloud processing device 5 remotely transmits a control command to the communication relay station 4, and the control command is further transmitted to the gas processing device to intelligently and selectively enable the gas processing device and control an operation time of the gas processing device so as to exchange the polluted gas in the indoor space A to the outdoor space and provide the purification of the polluted gas at the location of the gas processing device, thereby allowing the polluted gas at a location of the at least one gas processing device to be filtered and purified in real-time, thereby allowing the indoor gas detection data of the polluted gas in the indoor space to be decreased to a safety detection value, and allowing the polluted gas in the indoor space to be exchanged into a clean, safe, and breathable gas.

The cloud processing device 5 further comprises a gas molding flow simulation system (not shown) adapted to calculate the number of the gas processing device installed in the indoor space A, a gas flow field direction of the indoor space A, and the locations of gas pipelines and gas entrances and exits of the gas processing device for installing the gas processing device. The communication relay station 4 may be a mobile device or a router device. The mobile device can display the outdoor gas detection data, the indoor gas detection data, the device gas detection data so as to provide a notification in regards to a pollution condition in the indoor space A and a precaution of the polluted gas.

As described above, in one or some embodiments of the present disclosure, a cloud processing device 5 is provided to remotely transmit and intelligently compare the outdoor gas detection data, the indoor gas detection data, and the device gas device data of each of the devices with each other. Moreover, the communication relay station 4 transmits the control signal to the indoor gas exchange system 2, so as to allow the indoor gas exchange system 2 to intelligently and selectively control the gas exchange in the indoor space A, thereby allowing the indoor gas detection data of the polluted gas in the indoor space A decreased to a safety detection value and allowing the polluted gas in the indoor space A to be exchanged into a clean, safe, and breathable gas. The devices and the processes of the present disclosure are described in the following paragraphs.

The polluted gas may include at least one selected from the group consisting of particulate matters (PM1, PM2.5, PM10), carbon monoxide (CO), carbon dioxide ($CO_2$), ozone ($O_3$), sulfur dioxide ($SO_2$), nitrogen dioxide ($NO_2$), lead (Pb), total volatile organic compounds (TVOC), formaldehyde (HCHO), bacteria, fungi, and viruses, but not limited thereto.

As shown in FIG. 3 to FIG. 11, in one embodiment, the present disclosure provides a gas detection module 3. The gas detection module 3 includes a control circuit board 31, a gas detection main body 32, a microprocessor 33, and a communication device 34. The gas detection main body 32, the microprocessor 33, and the communication device 34 are integrally packaged with and electrically connected to the control circuit board 31. The microprocessor 33 and the communication device 34 are disposed on the control circuit board 31. The microprocessor 33 controls the driving signal of the gas detection main body 32 to enable the gas detection main body 32, receives the information of the polluted gas detected by the gas detection module 3 for computation and processing, communicates outwardly through the communication device 34, and converts the information into gas detection data for storage. The communication device 34 receives the gas detection data outputted from the microprocessor 33 and transmits the gas detection data to the indoor gas exchange system 2 or to an external device (which may be a mobile device (not shown)). Through enabling the indoor gas exchange system and controlling the air volume thereof, the polluted gas in the indoor space is filtered and thereby decreasing the indoor gas detection data to a safety detection value, and the polluted gas in the indoor space A can be exchanged into a being clean, safe, and breathable gas. Specifically, in this embodiment, the communication device 34 can be communicationally connected to the indoor gas exchange system 2 to transmit data to the indoor gas exchange system 2. According to the transmitted data the air volume and the number of the one-line indoor gas exchange system 2 may be adjusted through the gas detection module 3 according to a preset size of the indoor space A and an operation time for decreasing the indoor gas detection data of the polluted gas in the indoor space A to the safety detection value, but not limited thereto. Moreover, in some embodiments, the outwardly communication transmission of the communication devices 34 may be implemented through a bidirectional wired transmission. For example, the wired transmission may be achieved by a USB port, a mini-USB port, and micro-USB port. The outwardly communication transmission of the communication devices 34 may also be implemented through a bidirectional wireless transmission. For example, the wireless transmission may be achieved by a Wi-Fi module, a Bluetooth module, a radiofrequency identification module, and a near field communication module.

It is understood that, in the foregoing embodiment, the indoor gas detector 1b is placed in the indoor space A. The indoor gas detector 1b may be fixed in the indoor space A. In another embodiment, alternatively, the indoor gas detector 1b may be a portable detection device. In one embodiment, the indoor gas detector 1b may be a wearable device, such as a watch or a bracelet which can be worn on a human body (as shown in FIG. 1B to FIG. 1E). Therefore, when the user wearing the wearable device is in the indoor space A, the wearable device can detect the air pollution condition of the indoor space A anytime in real-time, such that the wearable device can transmit, record, and display the indoor gas detection data of the polluted gas in the indoor space A. Hence, in the case that the indoor gas detector 1b is a portable detection device, the communication device 34 of the gas detection module 3 of the indoor gas detector 1b can take advantages of the bidirectional wireless communication.

Please refer to FIG. 4A to FIG. 9A. The gas detection main body 32 includes a base 321, a piezoelectric actuator 322, a driving circuit board 323, a laser component 324, a particulate sensor 325, and an outer cap 326. The base 321 has a first surface 3211, a second surface 3212, a laser configuration region 3213, a gas inlet groove 3214, a gas-guiding component loading region 3215, and a gas outlet groove 3216. The first surface 3211 and the second surface 3212 are opposite to each other. The laser configuration region 3213 is hollowed out from the first surface 3211 to the second surface 3212. The outer cap 326 covers the base 321 and has a side plate 3261. The side plate 3261 has a gas inlet opening 3261a and a gas outlet opening 3261b. The gas inlet groove 3214 is recessed from the second surface 3212 and located adjacent to the laser configuration region 3213. The gas inlet groove 3214 has a gas inlet through hole 3214a and two lateral walls. The gas inlet through hole 3214a is in communication with outside of the base 321 and corresponds to the gas inlet opening 3261a of the outer cap 326. Two light permissive windows 3214b penetrate the two lateral walls of the gas inlet groove 3214 and are in communication with the laser configuration region 3213. Therefore, the first surface 3211 of the base 321 is covered by the outer cap 326, and the second surface 3212 of the base 321 is covered by the driving circuit board 323, so as to define a gas inlet path with the gas inlet groove 3214.

The gas-guiding component loading region 3215 is recessed from the second surface 3212 and in communication with the gas inlet groove 3214. A gas flowing hole 3215a penetrates a bottom surface of the gas-guiding component loading region 3215. Each of four corners of the gas-guiding component loading region 3215 has a positioning bump 3215b. The gas outlet groove 3216 has a gas outlet through hole 3216a, and the gas outlet through hole 3216a is corresponding to the gas outlet opening 3261b of the outer cap 326. The gas outlet groove 3216 includes a first region 3216b and a second region 3216c. The first region 3216b is recessed from a portion of the first surface 3211 corresponding to a vertical projection region of the gas-guiding component loading region 3215. The second region 3216c is at a portion extending from a portion not corresponding to the vertical projection region of the gas-guiding component loading region 3215, and the second region 3216c is hollowed out from the first surface 3211 to the second surface 3212 in a region where the first surface 3211 is not aligned with the gas-guiding component loading region 3215. The first region 3216b is connected to the second region 3216c to form a stepped structure. Moreover, the first region 3216b of the gas outlet groove 3216 is in communication with the gas flowing hole 3215a of the gas-guiding component loading region 3215, and the second region 3216c of the gas outlet groove 3216 is in communication with the gas outlet through hole 3216a. Therefore, when the first surface 3211 of the base 321 is covered by the outer cap 326 and the second surface 3212 of the base 321 is covered by the driving circuit board 323, the gas outlet groove 3216 and the driving circuit board 323 together define a gas outlet path.

The laser component 324 and the particulate sensor 325 are disposed on and electrically connected to the driving circuit board 323 and located in the base 321. Here, in order to clearly explain the positions of the laser component 324, the particulate sensor 325, and the base 321, the driving circuit board 323 is not illustrated. The laser component 324 is received in the laser configuration region 3213 of the base 321. The particulate sensor 325 is received in the gas inlet groove 3214 of the base 321 and aligned with the laser component 324. Moreover, the laser component 324 corresponds to the light permissive windows 3214b. The light permissive windows 3214b allow the light beam emitted by the laser component 324 to pass therethrough, so that the light beam may further enter into the gas inlet groove 3214. The path of the light beam emitted by the laser component 324 passes through the light permissive windows 3214b and is orthogonal to the gas inlet groove 3214. The light beam emitted by the laser component 324 enters into the gas inlet groove 3214 through the light permissive windows 3214b, and the particulate matters in the gas in the gas inlet groove 3214 is illuminated by the light beam. When the light beam encounters the particulate matters, the light beam will be scattered to generate light spots. Hence, the particulate sensor 325 receives and calculates the light spots generated by the scattering, such that the particulate sensor 325 can obtain the detection data of the gas. Furthermore, a gas sensor 327a is disposed on and electrically connected to the driving circuit board 323, and is received in the gas inlet groove 3214 for detecting the polluted gas introduced into the gas inlet groove 3214. In one embodiment of the present disclosure, the gas sensor 327a includes at least one selected from the group consisting of a volatile organic compound detector capable of detecting gas information of carbon dioxide ($CO_2$) or total volatile organic compounds (TVOC), a formaldehyde sensor capable of detecting gas information of formaldehyde (HCHO) gas, a bacterial sensor capable of detecting information of bacteria or fungi, and a virus sensor capable of detecting information of viruses.

The piezoelectric actuator 322 is received in the square-shaped gas-guiding component loading region 3215 of the base 321 in communication with the gas inlet groove 3214. When the piezoelectric actuator 322 operates, the gas in the gas inlet groove 3214 is drawn into the piezoelectric actuator 322, passing through the gas flowing hole 3215a of the gas-guiding component loading region 3215, and entering into the gas outlet groove 3216. Moreover, the driving circuit board 323 covers the second surface 3212 of the base 321. The laser component 324 is disposed on and electrically connected to the driving circuit board 323, and the particulate sensor 325 is also disposed on and electrically connected to the driving circuit board 323. As the outer cap 326 covers the base 321, the gas inlet opening 3216a is corresponding to the gas inlet through hole 3214a of the base 321, and the gas outlet opening 3216b is corresponding to the gas outlet through hole 3216a of the base 321.

The piezoelectric actuator 322 includes a nozzle plate 3221, a chamber frame 3222, an actuation body 3223, an insulation frame 3224, and a conductive frame 3225. The nozzle plate 3221 is made of a flexible material and has a suspension sheet 3221a and a hollow hole 3221b. The suspension sheet 3221a is a flexible sheet which can bend and vibrate. The shape and the size of the suspension sheet 3221a approximately correspond to those of the inner edge of the gas-guiding component loading region 3215. The hollow hole 3221b penetrates through the center portion of the suspension sheet 3221a for allowing the gas flowing therethrough. In one embodiment, the shape of the suspension sheet 3221a may be one of square, circle, ellipse, triangle, and polygon.

The chamber frame 3222 is stacked on the nozzle plate 3221, and the shape of the chamber frame 3222 is corresponding to the shape of the nozzle plate 3221. The actuation body 3223 is stacked on the chamber frame 3222. A resonance chamber 3226 is defined between the actuation body 3223, the nozzle plate 3221, and the suspension sheet 3221a. The insulation frame 3224 is stacked on the actuation body 3223. The appearance of the insulation frame 3224 is similar to the appearance of the nozzle plate 3221. The conductive frame 3225 is stacked on the insulation frame 3224. The appearance of the conductive frame 3225 is similar to the appearance of the insulation frame 3224. The conductive frame 3225 has a conductive frame pin 3225a and a conductive electrode 3225b. The conductive frame pin 3225a extends outwardly from the outer edge of the conductive frame 3225, and the conductive electrode 1225b extends inwardly from the inner edge of the conductive frame 3225. Moreover, the actuation body 3223 further includes a piezoelectric carrier plate 3223a, an adjusting resonance plate 3223b, and a piezoelectric plate 3223c. The piezoelectric carrier plate 3223a is stacked on the chamber frame 3222. The adjusting resonance plate 3223b is stacked on the piezoelectric carrier plate 3223a. The piezoelectric plate 3223c is stacked on the adjusting resonance plate 3223b. The adjusting resonance plate 3223b and the piezoelectric plate 3223c are accommodated in the insulation frame 3224. The conductive electrode 3225b of the conductive frame 3225 is electrically connected to the piezoelectric plate 3223c. In one embodiment, the piezoelectric carrier plate 3223a and the adjusting resonance plate 3223b are both made of the same conductive material or different conductive materials. The piezoelectric carrier plate 3223a has a piezoelectric pin 3223d. The piezoelectric pin 3223d and the conductive frame pin 3225a are in electrical connection with a driving circuit (not shown) of the driving circuit board 323 to receive a driving signal (which may be a driving frequency and a driving voltage). The piezoelectric pin 3223d, the piezoelectric carrier plate 3223a, the adjusting resonance plate 3223b, the piezoelectric plate 3223c, the conductive electrode 3225b, the conductive frame 3225, and the conductive frame pin 3225a may together form a circuit for transmitting the driving signal, and the insulation frame 3224 is provided for electrically isolating the conductive frame 3225 from the actuation body 3223 for avoiding short circuit, thereby the driving signal can be transmitted to the piezoelectric plate 3223c. When the piezoelectric plate 3223c receives the driving signal, the piezoelectric plate 3223c deforms owing to the piezoelectric effect, and thus the piezoelectric carrier plate 3223a and the adjusting resonance plate 3223b are driven to perform reciprocating vibration correspondingly.

Moreover, the adjusting resonance plate 3223b is disposed between the piezoelectric plate 3233c and the piezoelectric carrier plate 3223a as a cushion element so as to adjust the vibration frequency of the piezoelectric carrier plate 3223a. Generally, the thickness of the adjusting resonance plate 3223b is greater than the thickness of the piezoelectric carrier plate 3223a. The thickness of the adjusting resonance plate 3223b may be changed to adjust the vibration frequency of the actuation body 3223.

Figure 7A:
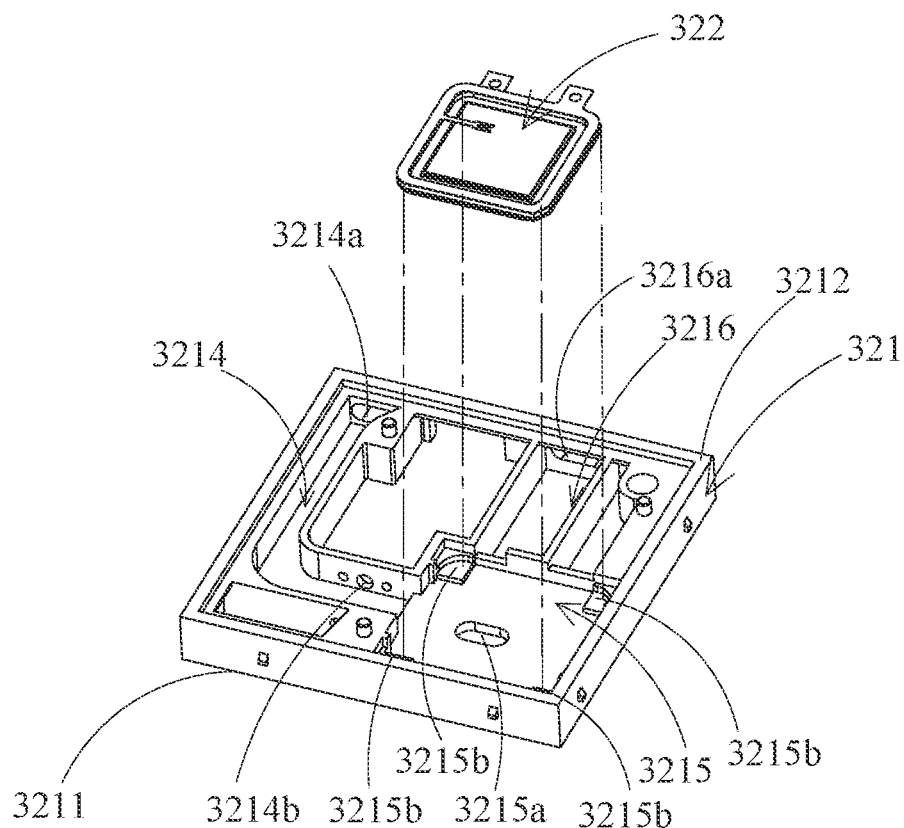
FIG. 7A illustrates an exploded view showing that a piezoelectric actuator is to be disposed in the base, according to the exemplary embodiment of the present disclosure.
Figure 7B:
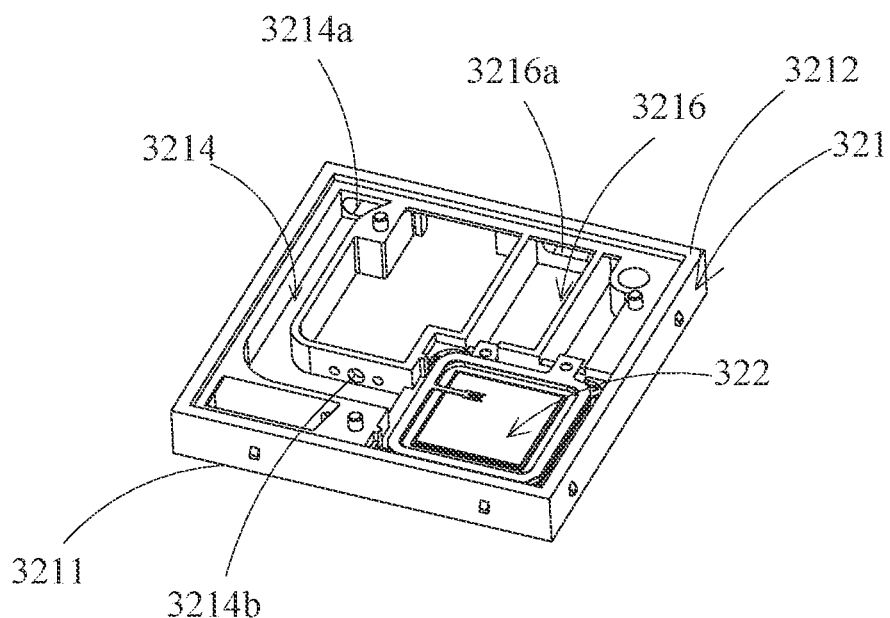
FIG. 7B illustrates a perspective view showing that the piezoelectric actuator is disposed in the base, according to the exemplary embodiment of the present disclosure.
Figure 8A:
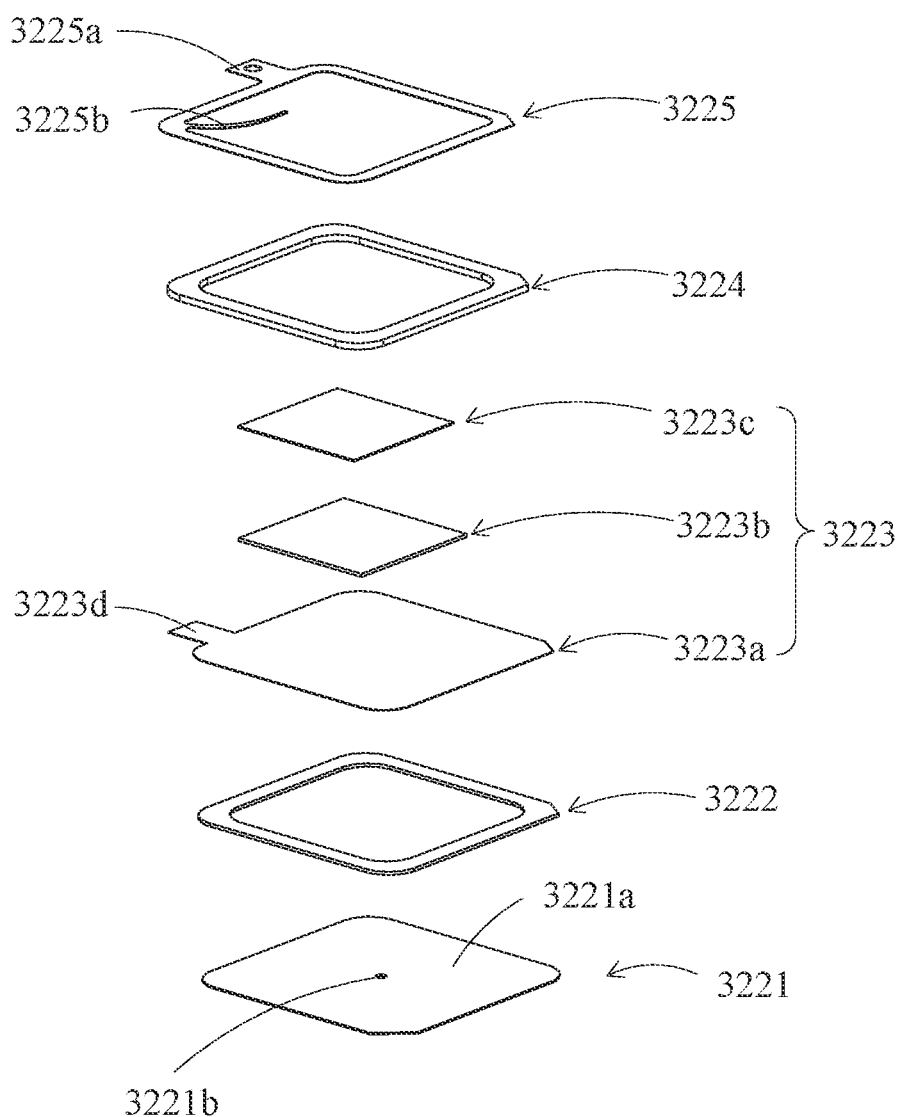
FIG. 8A illustrates an exploded view (1) of the piezoelectric actuator of the exemplary embodiment of the present disclosure.
Figure 8B:
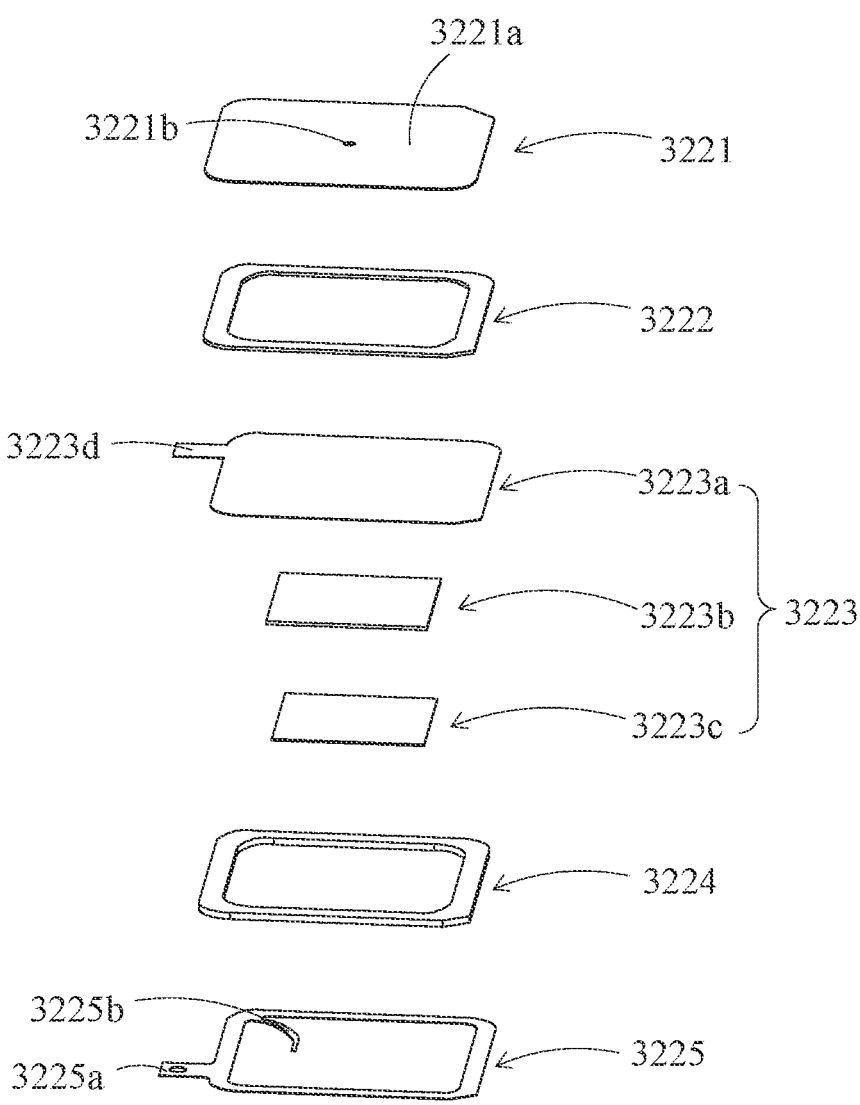
FIG. 8B illustrates an exploded view (2) of the piezoelectric actuator of the exemplary embodiment of the present disclosure.

Please refer to FIG. 7A. FIG. 7B, FIG. 8A, FIG. 8B, and FIG. 9A. The nozzle plate 3221, the chamber frame 3222, the actuation body 3223, the insulation frame 3224, and the conductive frame 3225 are sequentially stacked and assembled, so as to provide a piezoelectric actuator 322 placed and positioned in the gas-guiding component loading region 3215, so that a clearance 3221c is defined between the suspension sheet 3221a and the inner edge of the gas-guiding component loading region 3215 for the gas to pass therethrough. A gas flow chamber 3227 is formed between a bottom of the nozzle plate 3221 and the bottom surface of the gas-guiding component loading region 3215. The gas flow chamber 3227 is in communication with, through the hollow hole 3221b of the nozzle plate 3221, the resonance chamber 3226 formed between the actuation body 3223, the nozzle plate 3221, and the suspension sheet 3221a. Through controlling the vibration frequency of the gas in the resonance chamber 3226 and making the vibration frequency of the gas in the resonance chamber 3226 nearly the same with the vibration frequency of the suspension sheet 3221a, the resonance chamber 3226 and the suspension sheet 3221a can generate the Helmholtz resonance effect so as to improve the transmission efficiency of the gas. When the piezoelectric plate 3223c moves in a direction away from the bottom surface of the gas-guiding component loading region 3215, the piezoelectric plate 3223c drives the suspension sheet 3221a of the nozzle plate 3221 to move in the direction away from the bottom surface of the gas-guiding component loading region 3215 correspondingly. Hence, the volume of the gas flow chamber 3227 expands dramatically, so that the internal pressure of the gas flow chamber 3227 decreases and creates a negative pressure, thereby drawing the gas outside the piezoelectric actuator 322 to flow into the piezoelectric actuator 322 through the clearance 3221c and enter into the resonance chamber 3226 through the hollow hole 3221b, thereby increasing the gas pressure of the resonance chamber 3226 and thus generating a pressure gradient. When the piezoelectric plate 3223c drives the suspension sheet 3221a of the nozzle plate 3221 to move toward the bottom surface of the gas-guiding component loading region 3215, the gas inside the resonance chamber 3226 is pushed to flow out quickly through the hollow hole 3221b so as to further push the gas inside the gas flow chamber 3227, thereby the converged gas can be quickly and massively ejected out of the gas flow chamber 3227 and introduced into the gas flowing hole 3215a of the gas-guiding loading region 321 in a state closing to an ideal gas state under the Benulli's law.

Figure 9A:
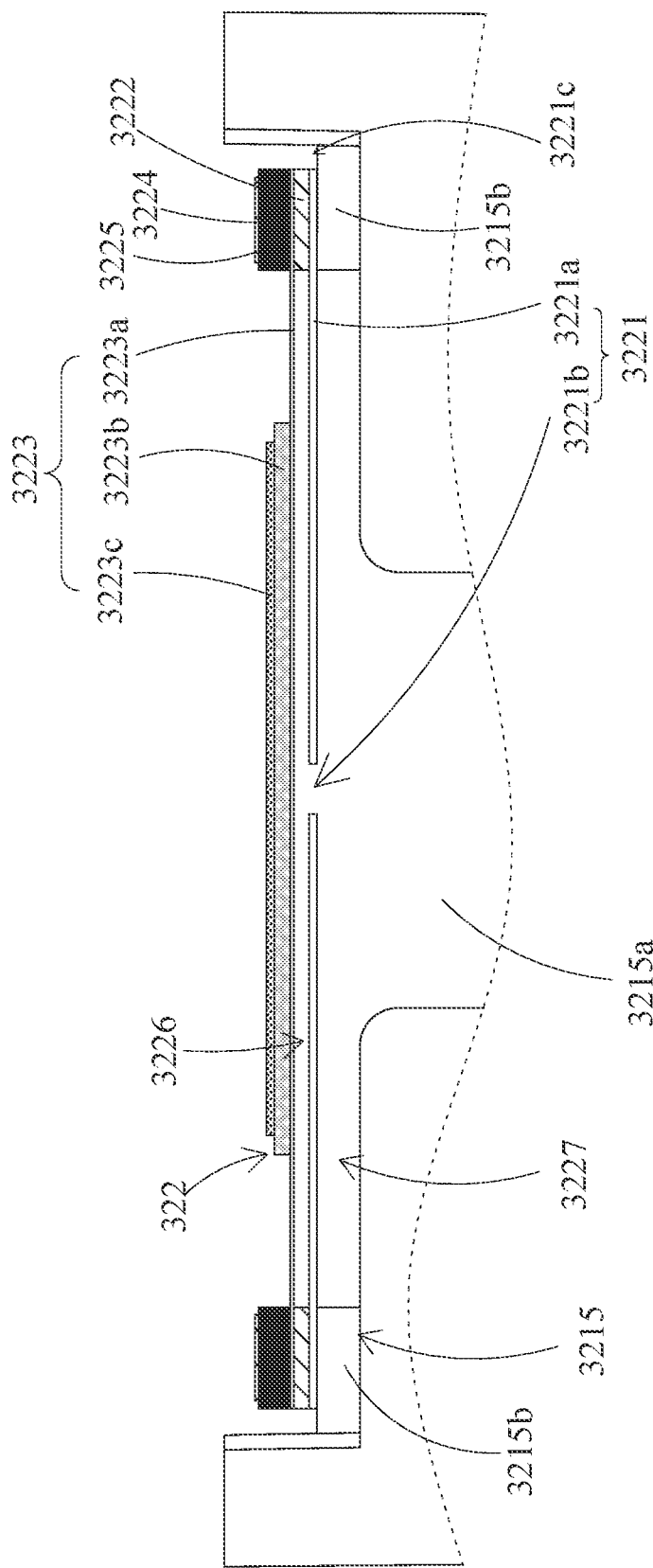
FIG. 9A illustrates a cross-sectional view (1) showing the operation of the piezoelectric actuator of the exemplary embodiment of the present disclosure.
Figure 9B:
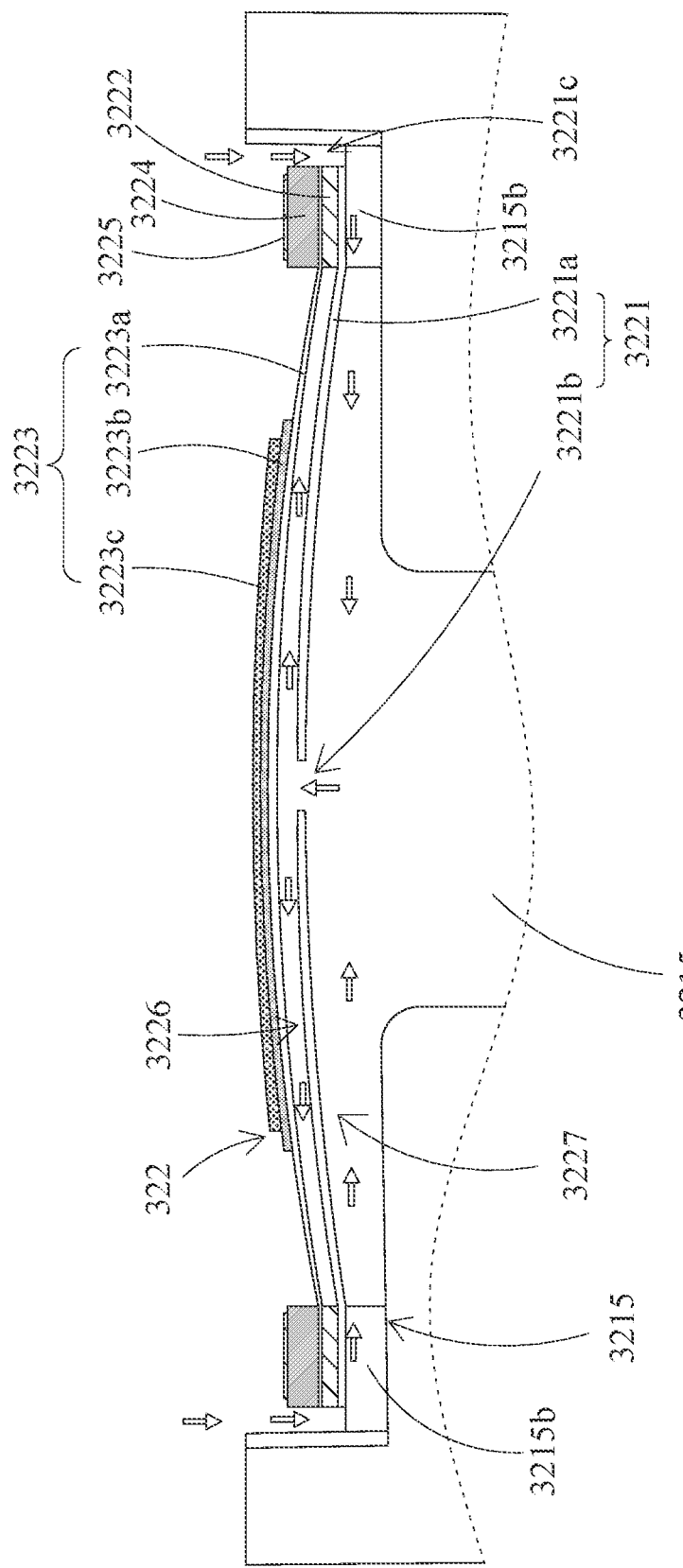
FIG. 9B illustrates a cross-sectional view (2) showing the operation of the piezoelectric actuator of the exemplary embodiment of the present disclosure.
Figure 9C:
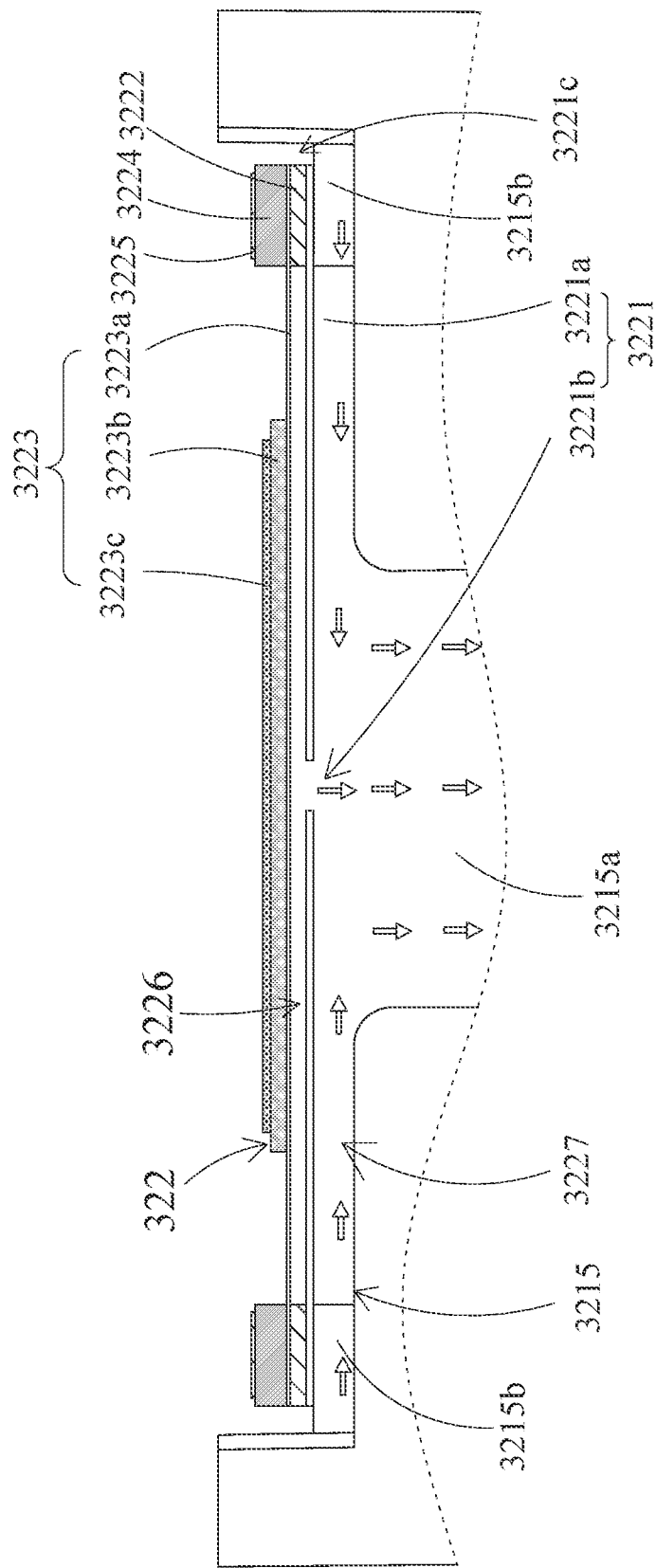
FIG. 9C illustrates a cross-sectional view (3) showing the operation of the piezoelectric actuator of the exemplary embodiment of the present disclosure.
Figure 10A:
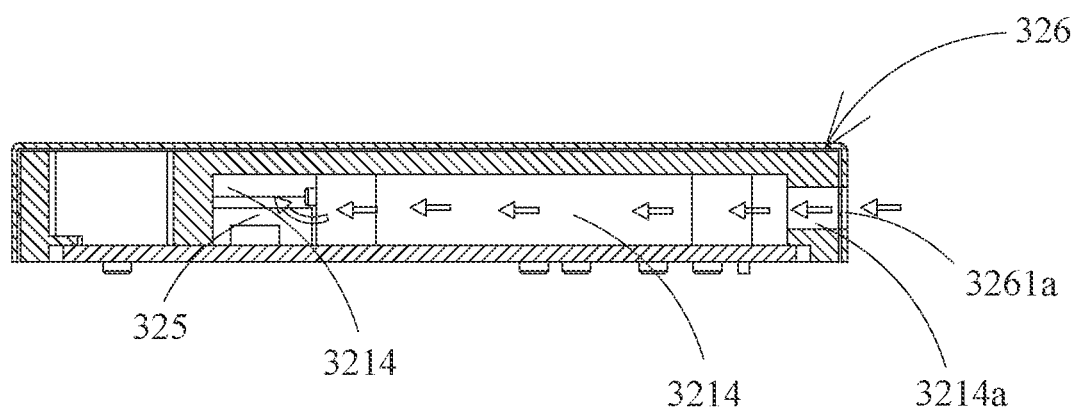
FIG. 10A illustrates a cross-sectional view (1) showing the operation of the gas detection module of the exemplary embodiment of the present disclosure.
Figure 10B:
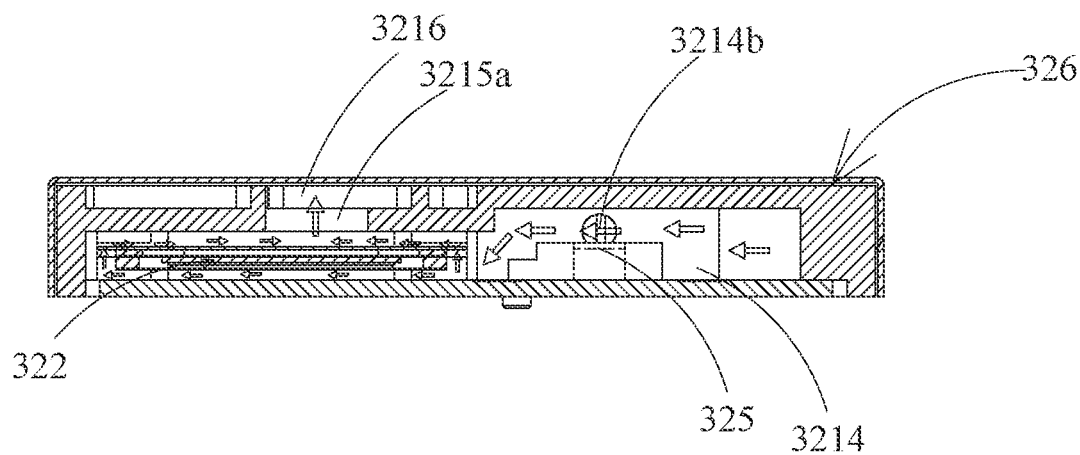
FIG. 10B illustrates a cross-sectional view (2) showing the operation of the gas detection module of the exemplary embodiment of the present disclosure.
Figure 10C:
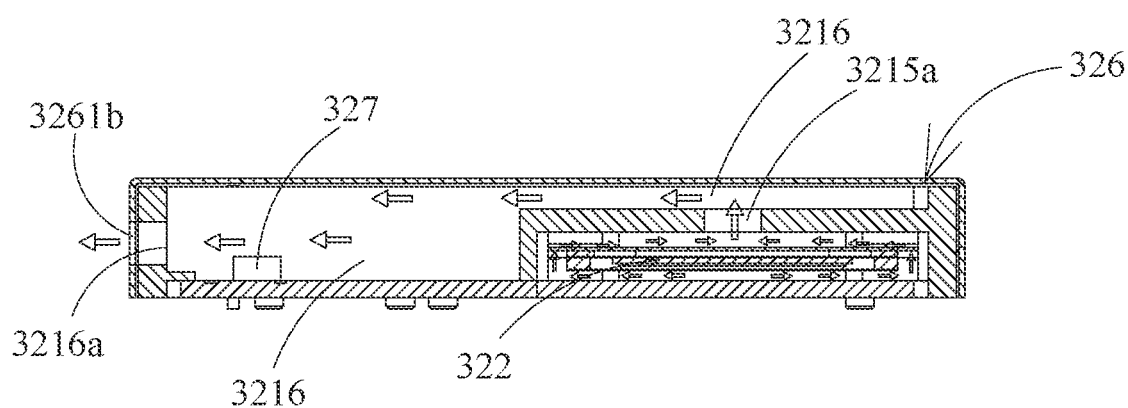
FIG. 10C illustrates a cross-sectional view (3) showing the operation of the gas detection module of the exemplary embodiment of the present disclosure.
Figure 11:
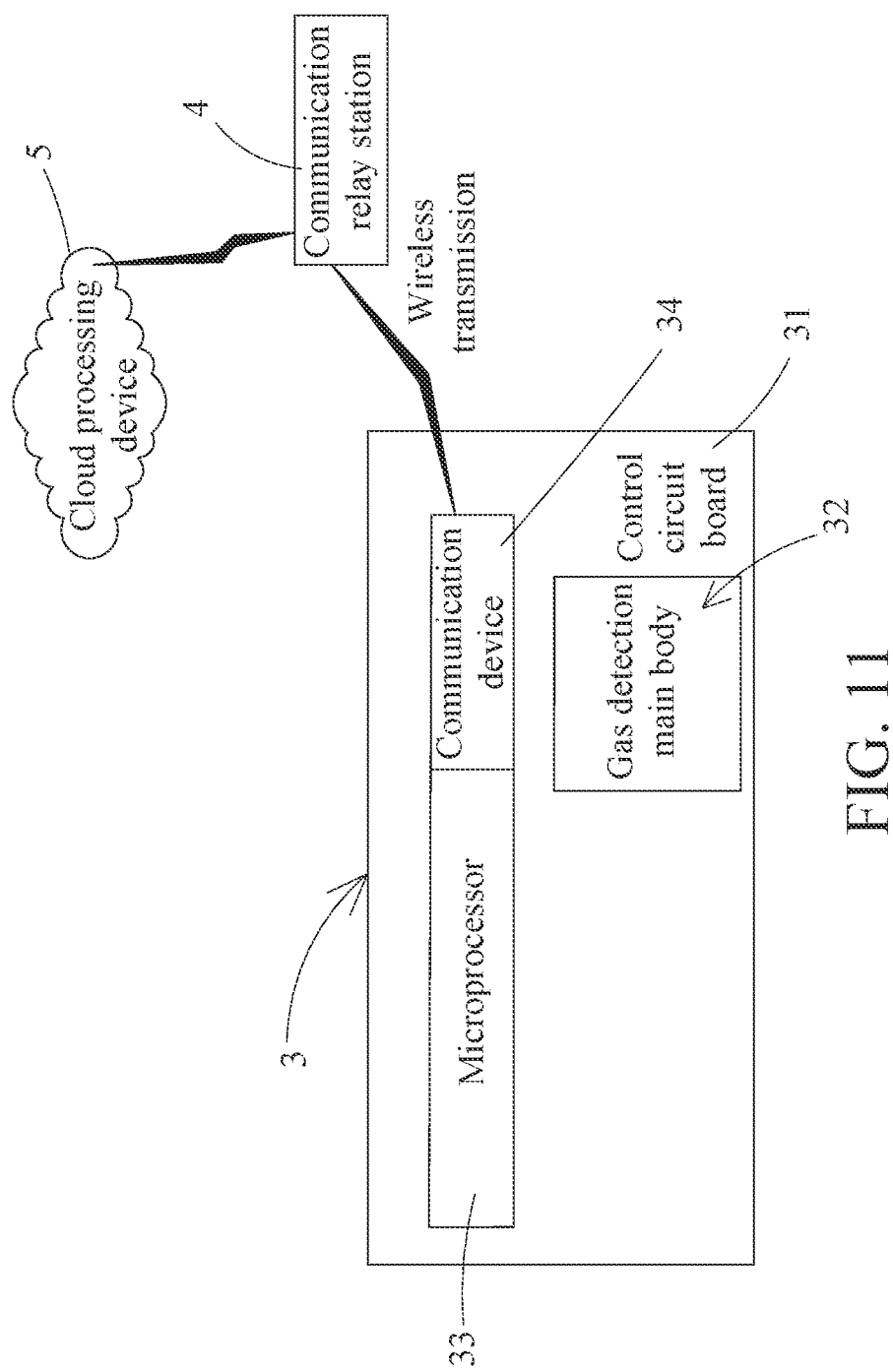
FIG. 11 illustrates a block diagram showing the signal transmission of the gas detection module and the communication relay station.

Therefore, through repeating the steps as shown in FIG. 9B and FIG. 9C, the piezoelectric plate 3223c can bend and vibrate reciprocatingly. Further, after the gas is discharged out of the resonance chamber 3226, the internal pressure of the resonance chamber 3226 is lower than the equilibrium pressure due to the inertia, as a result, the pressure difference guides the gas outside the resonance chamber 3226 into the resonance chamber 3226 again. Thus, through controlling the vibration frequency of the gas inside the resonance chamber 3226 to be nearly the same with the vibration frequency of the piezoelectric plate 3223c to generate the Helmholtz resonance effect, high-speed and large-volume gas transmission can be achieved. As shown in FIGS. 10A to 10C, the gas enters into the gas detection main body 3 from the gas inlet opening 3214a of the outer cap 326, passes through the gas inlet through hole 3214a and enters into the gas inlet groove 3214 of the base 321, and flows to the particulate sensor 325. Furthermore, the piezoelectric actuator 322 continuously draws the gas in the gas inlet path so as to facilitate the gas outside the gas detection main body 3 to be introduced inside quickly and to pass stably through the particulate sensor 325. Next, the light beam emitted by the laser component 324 passes through the light permissive windows 3214b and enters into the gas inlet groove 3214. The gas in the gas inlet groove 3214 passing through the particulate sensor 325 is illuminated by the light beam. When the light beam encounters the particulate matters in the gas, the light beam will be scattered to generate light spots. The particulate sensor 325 receives and calculates the light spots generated by the scattering, such that the particulate sensor 325 obtains the information in regard to the particle size and the concentration of the particulate matters in the gas. Moreover, the gas passing through the particulate sensor 325 is continuously introduced into the gas flowing hole 3215a of the gas-guiding component loading region 3215 by the driving of the piezoelectric actuator 122 and enters into the gas outlet groove 1216. Last, after the gas enters into the gas outlet groove 3216, since the piezoelectric actuator 322 continuously delivers the gas into gas outlet groove 3216, the gas in the gas outlet groove 3216 is pushed and eventually discharged out of the gas detection main body 3 through the gas outlet through hole 3216a and the gas outlet opening 3261b.

As noted above, in one or some embodiments of the present disclosure, the outdoor gas detector 1a and the indoor gas detector 1b not only can detect the particulate matters in the gas, but also can detect the gas characteristics of the introduced gas, for example, to determine whether the gas is formaldehyde, ammonia, carbon monoxide, carbon dioxide, oxygen, ozone, or the like. Therefore, in one or some embodiments, each of the outdoor gas detector 1a and the indoor gas detector 1b further includes a gas sensor 327a disposed on and electrically connected to the driving circuit board 323 and received in the gas outlet groove 3216. The gas sensor 327a is adapted to detect the concentration and/or the characteristics of the volatile organic compound contained in the gas export from the gas outlet groove 3216.

Figure 2:
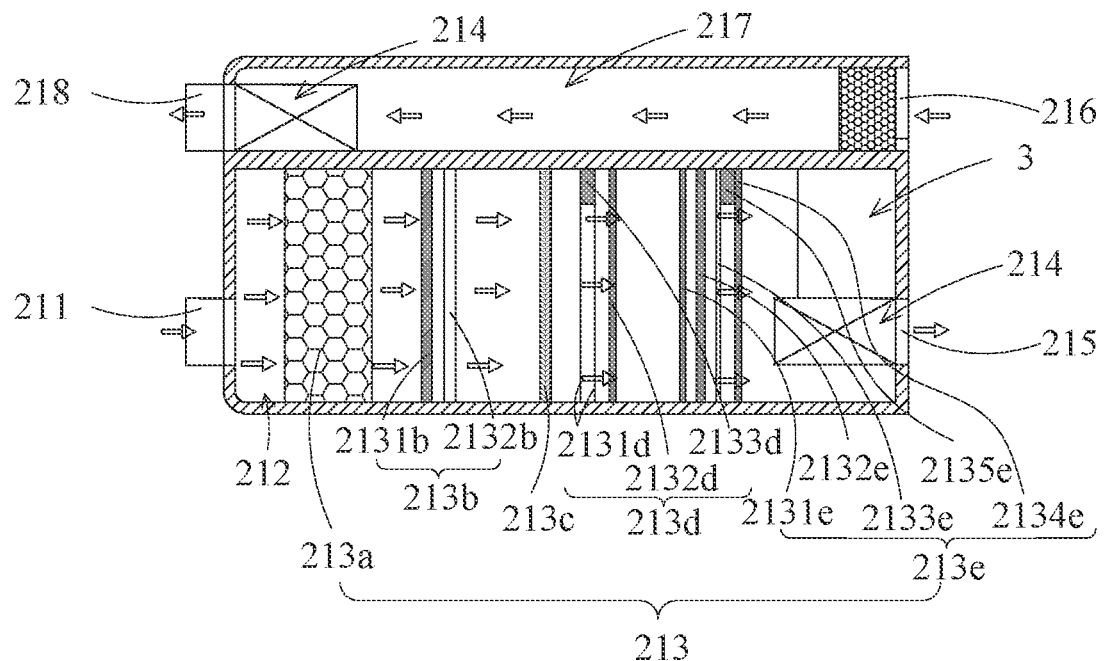
FIG. 2 illustrates a cross-sectional view of a gas exchanger of the exemplary embodiment of the present disclosure.
Figure 3:
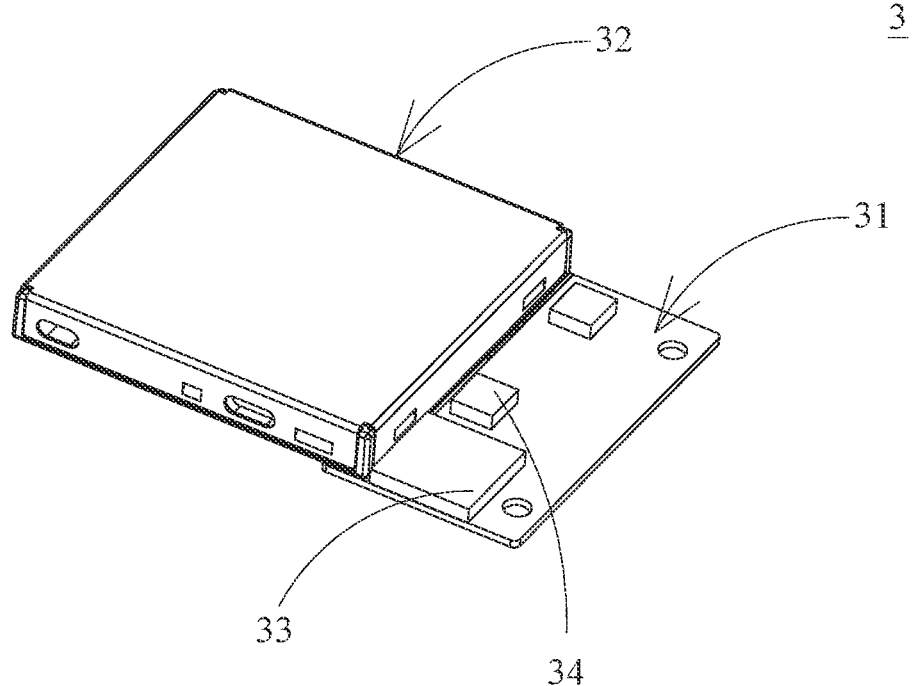
FIG. 3 illustrates a perspective view of a gas detection module of the exemplary embodiment of the present disclosure.
Figure 4A:
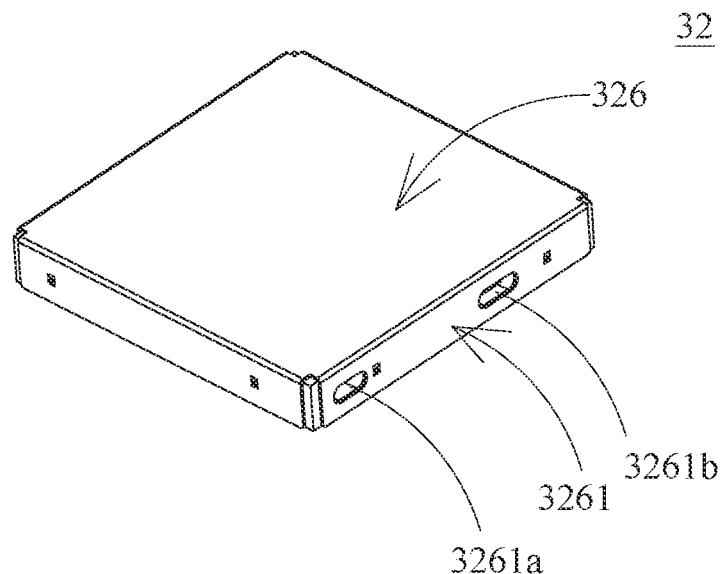
FIG. 4A illustrates a perspective view (1) of the gas detection module of the exemplary embodiment of the present disclosure.
Figure 4B:
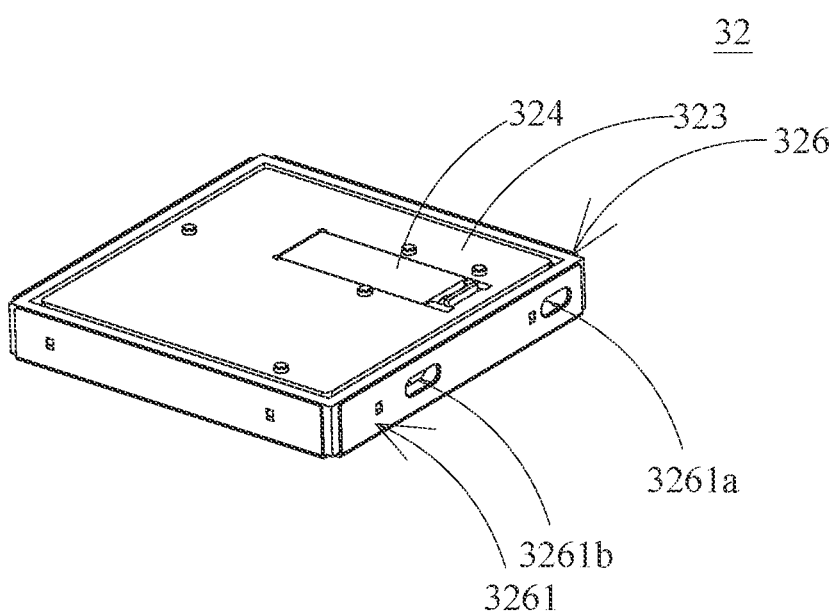
FIG. 4B illustrates a perspective view (2) of the gas detection module of the exemplary embodiment of the present disclosure.
Figure 4C:
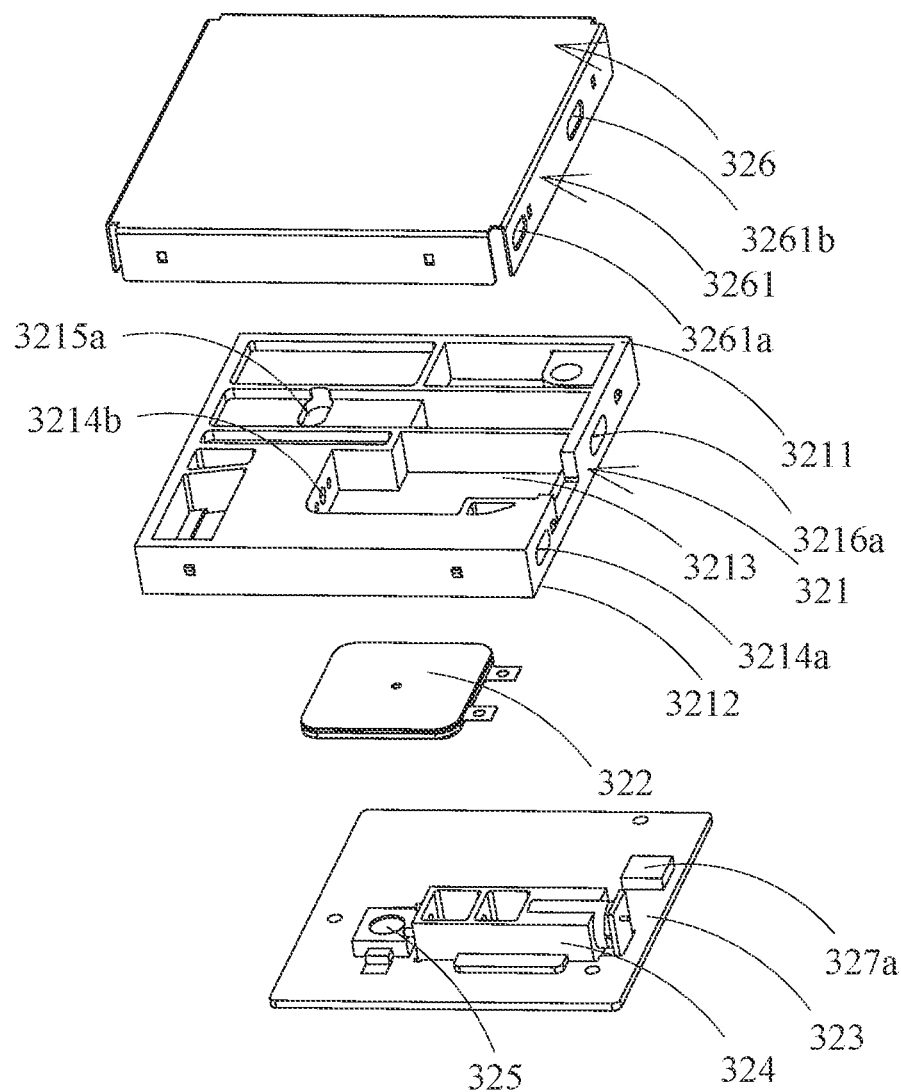
FIG. 4C illustrates an exploded view of the gas detection module of the exemplary embodiment of the present disclosure.
Figure 5A:
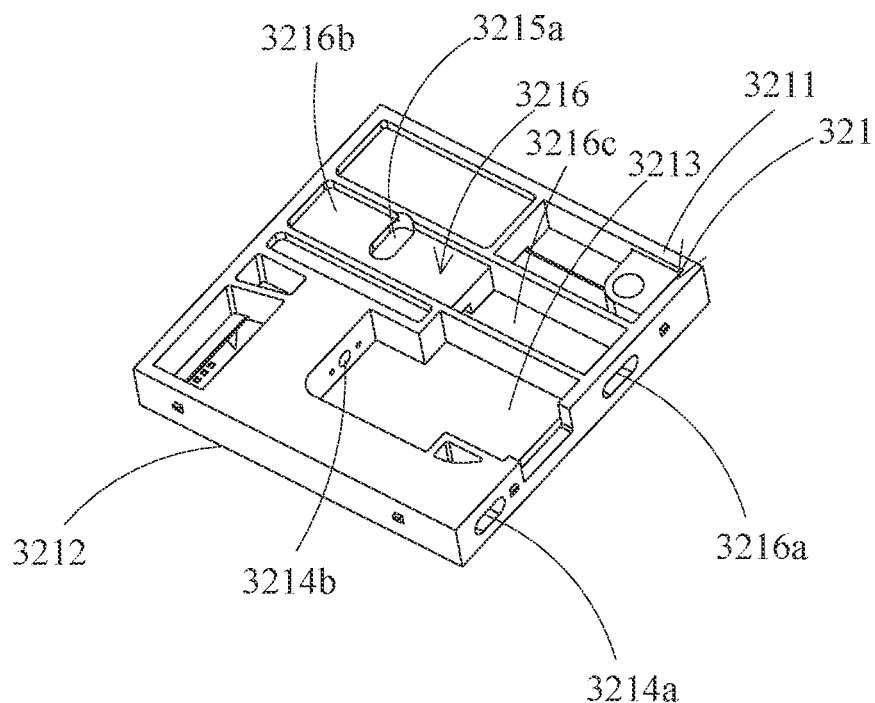
FIG. 5A illustrates a perspective view (1) of the base of the exemplary embodiment of the present disclosure.
Figure 5B:
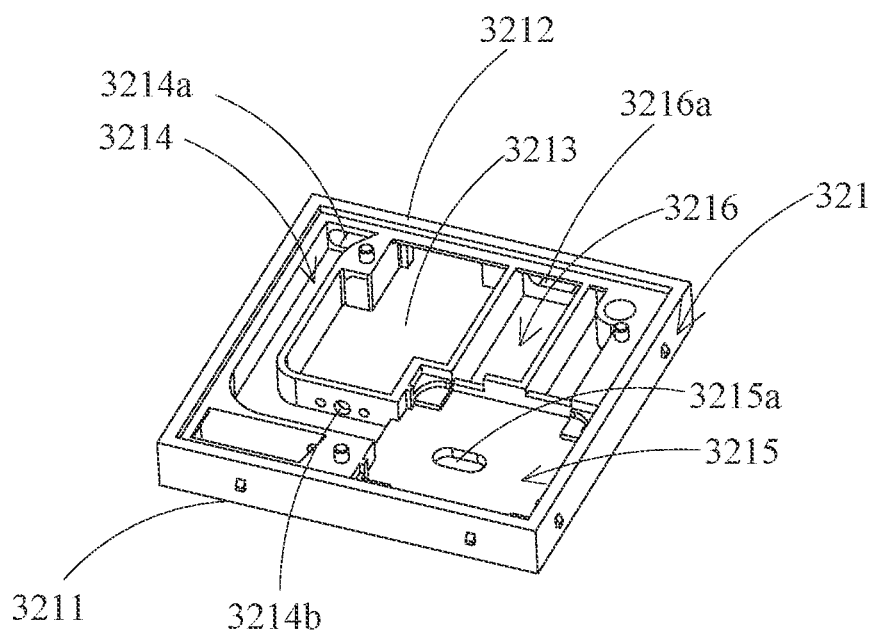
FIG. 5B illustrates a perspective view (2) of the base of the exemplary embodiment of the present disclosure.
Figure 6:
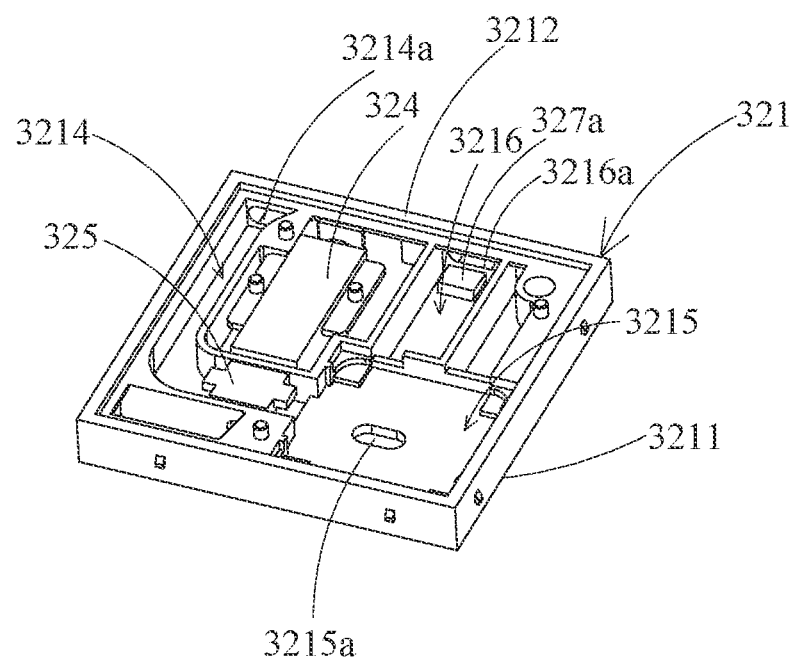
FIG. 6 illustrates a perspective view (3) of the base of the exemplary embodiment of the present disclosure.

Please refer to FIG. 2. The gas processing device 2 is a gas exchanger 21, and the gas exchanger 21 includes at least one gas inlet 211, an inlet channel 212, a cleaning unit 213, at least one flow-guiding component 214, at least one gas outlet 215, at least one gas-exchange inlet 216, a gas-exchange channel 217, and at least one gas-exchange outlet 218. The gas exchanger 21 further comprises a gas detection module 3 to enable the flow-guiding component 214 and introduce the outdoor gas into the gas exchanger 21. The at least one gas inlet 211 is connected to the inlet channel 212. The cleaning unit 213 is disposed in the inlet channel 212 for filtering and purifying the gas introduced from the at least one gas inlet 211. The at least one gas outlet 215 is in communication with the inlet channel 212 and is connected to the at least one flow-guiding component 214 for introducing the filtered and purified gas from the at least one gas outlet 215 into the indoor space A. The at least one gas-exchange inlet 216 is connected to the gas-exchange channel 217, and the gas-exchange channel 217 is in communication with the at least one gas-exchange outlet 218. The communication device 34 of the gas detection module 3 receives the control command transmitted by the communication relay station 4 to intelligently and selectively controls the introduction of the outdoor gas into the indoor space A, so that the polluted gas in the indoor space A is exchanged with the outdoor gas, thereby allowing the indoor gas detection data of the polluted gas in the indoor space A to be decreased to the safety detection value.

In this embodiment, when the cloud processing device 5 receives and compares the indoor gas detection data with the outdoor gas detection data and determines that the outdoor gas detection data is better than the indoor gas detection data, the cloud processing device 5 remotely transmits the control command to the communication relay station 4, and the control command is further transmitted to the gas detection module 3 of the gas exchanger 21 to intelligently and selectively enable the gas exchanger 21 and control an operation time of the gas exchanger 21, so that the flow-guiding component 214 is enabled to introduce the outdoor gas into the inlet channel 212 from the at least one gas inlet 211, pass through the cleaning unit 213 for filtering and purifying, and introduce into the at least one gas outlet 215 to enter into the indoor space A, and the polluted gas in the indoor space A is introduced into the gas-exchange channel 217 from the at least one gas-exchange inlet 216 and discharged to the outdoor space from the at least one gas-exchange outlet 218. Hence, the polluted gas in the indoor space A can be exchanged to the outdoor space and the polluted gas at the location of the gas exchanger 21 can be purified in real-time, thereby allowing the indoor gas detection data of the polluted gas in the indoor space A to be decreased to the safety detection value.

In this embodiment, when the cloud processing device 5 receives and compares the indoor gas detection data with the outdoor gas detection data and determines that the indoor gas detection data is better than the outdoor gas detection data, the cloud processing device 5 remotely transmits the control command to the communication relays station 4, and the control command is further transmitted to the gas detection module 3 of the gas exchanger 21 to intelligently and selectively disable the gas exchanger 21, so that the outdoor gas is not introduced into the indoor space A, thereby allowing the indoor gas detection data of the polluted gas in the indoor space A to be decreased to the safety detection value.

Figure 1B:
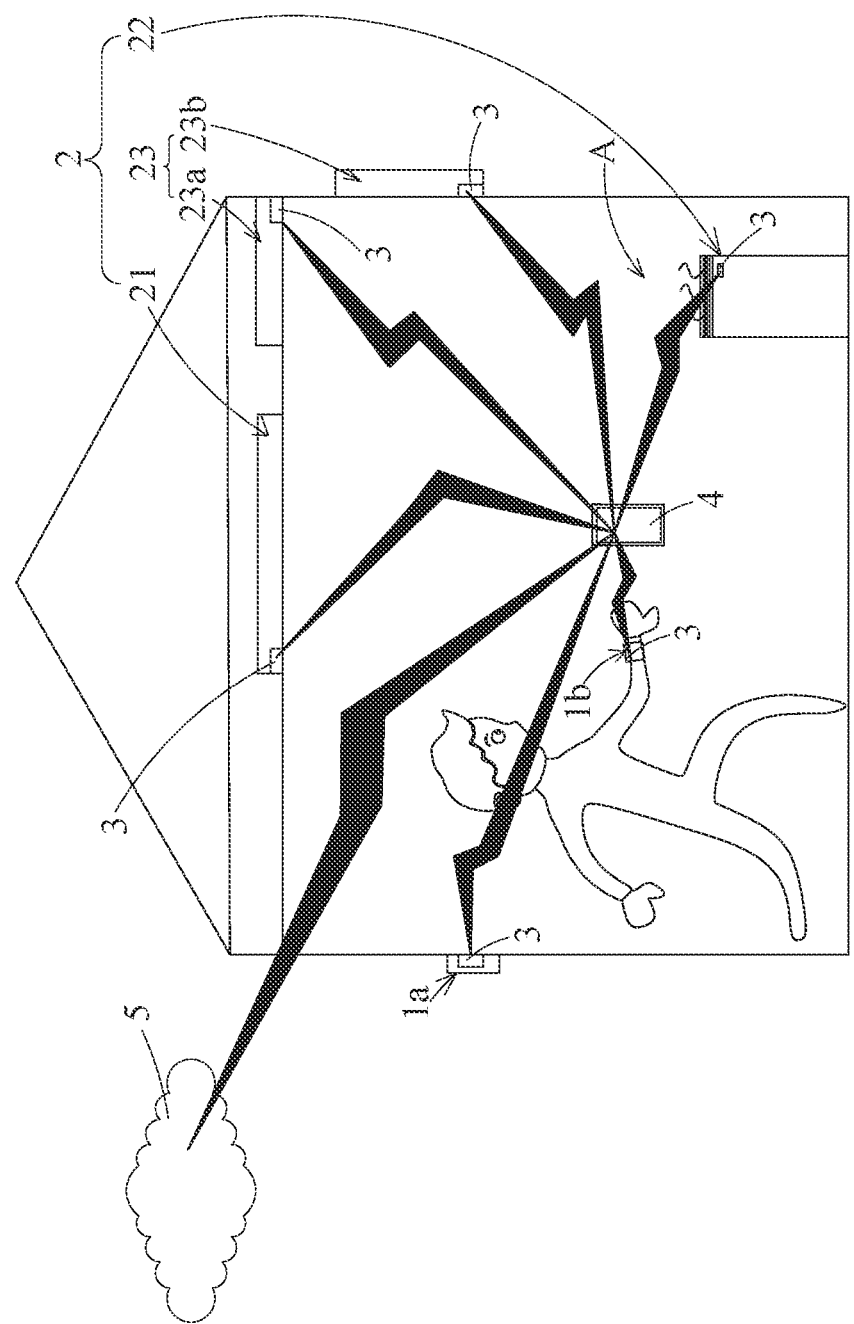
FIG. 1B illustrates a schematic view (1) for the operation of the method for preventing and handling indoor air pollution of the exemplary embodiment of the present disclosure.

Please refer to FIG. 1B. In one embodiment, the gas processing device is a cleaner 22. The cleaner 22 includes the gas detection module 3, and the microprocessor 33 of the gas detection module 3 is adapted to output a device gas detection data of the cleaner 22 to the communication device 34 to wirelessly transmit the device gas detection data to the communication relay station 4, and the device gas detection data is further transmitted to the cloud processing device 5 for storage and intelligent computation and comparison. When the device gas detection data of the cleaner 22 is indicates that the air in the location of the cleaner 22 is polluted (namely, the location of the cleaner 22 is in a polluted state), the cloud processing device 5 remotely transmits the control command to the communication relay station 4, and the control command is further transmitted to the gas detection module 3 of the cleaner 22, so that the gas detection module 3 intelligently and selectively enable the cleaner 22 and control an operation time of the cleaner 22, thereby allowing the polluted gas at the location of the cleaner 22 to be filtered and purified in real-time and allowing the indoor gas detection data of the polluted gas in the indoor space A to be decreased to the safety detection value.

Furthermore, when the cloud processing device 5 compares the indoor gas detection data with the outdoor gas detection data and determines that the indoor gas detection data is better than the outdoor gas detection data, and when the device gas detection data of the cleaner 22 indicates that the location of the cleaner 22 is in the polluted state, the cloud processing device 5 remotely transmits the control command to the communication relay station 4, and the control command is further transmitted to the gas detection module 3 of the gas exchanger 21 and the gas detection module 3 of the cleaner 22, so as to intelligently and selectively disable the gas exchanger 21 so that the outdoor gas is not introduced into the indoor space A, and to intelligently and selectively enable the cleaner 22 and control the operation time of the cleaner 22 so that the polluted gas at the location of the cleaner 22 can be filtered and purified in real-time, thereby allowing the indoor gas detection data of the polluted gas in the indoor space A to be decreased to the safety detection value. The gas detection module 3 of the cleaner 22 is adapted to output a reminder as an indication for replacing filtering consumables of the cleaner 22.

Please refer to FIG. 1B. In one embodiment, the gas processing device is an air conditioner 23 (which may be a central air conditioner 23a or an individual air conditioner 23b). The air conditioner 23 includes the gas detection module 3, and the microprocessor 33 of the gas detection module 3 is adapted to output a device gas detection data of the air conditioner 23 to the communication device 34 to wirelessly transmit to the communication relay station 4, and the device gas detection data is further transmitted to the cloud processing device 5 for storage and intelligent computation and comparison. When the device gas detection data of the air conditioner 23 indicates that a location of the air conditioner 23 is in a polluted state, the cloud processing device 5 remotely transmits the control command to the communication relay station 4, and the control command is further transmitted to the gas detection module 3 of the air conditioner 23 to intelligently and selectively enable the air conditioner 23 and control an operation time of the air conditioner 23, so that the polluted gas at the location of the air conditioner 23 is filtered and purified in real-time and adjust a temperature, a humidity, and a gas flow in the indoor space A, thereby allowing the indoor gas detection data of the polluted gas in the indoor space A to be decreased to the safety detection value.

Furthermore, when the cloud processing device 5 compares the indoor gas detection data with the outdoor gas detection data and determines that the indoor gas detection data is better than the outdoor gas detection data, and when the device gas detection data of the air conditioner 23 indicates that the location of the air conditioner 23 is in the polluted state, the cloud processing device 5 remotely transmits the control command to the communication relay station 4, and the control command is further transmitted to the gas detection module 3 of the gas exchanger 21 and the gas detection module 3 of the air conditioner 23, so as to intelligently and selectively disable the gas exchanger 21 so that the outdoor gas is not introduced into the indoor space A, and intelligently and selectively enable the air conditioner 23 and control the operation time of the air conditioner 23 so that the polluted gas at the location of the air conditioner 23 is filtered and purified in real-time and adjust the temperature, the humidity, and the gas flow in the indoor space A, thereby allowing the indoor gas detection data of the polluted gas in the indoor space A to be decreased to the safety detection value. The gas detection module 3 of the air conditioner 23 is adapted to output a reminder as an indication for replacing filtering consumables of the air conditioner 23.

Figure 1C:
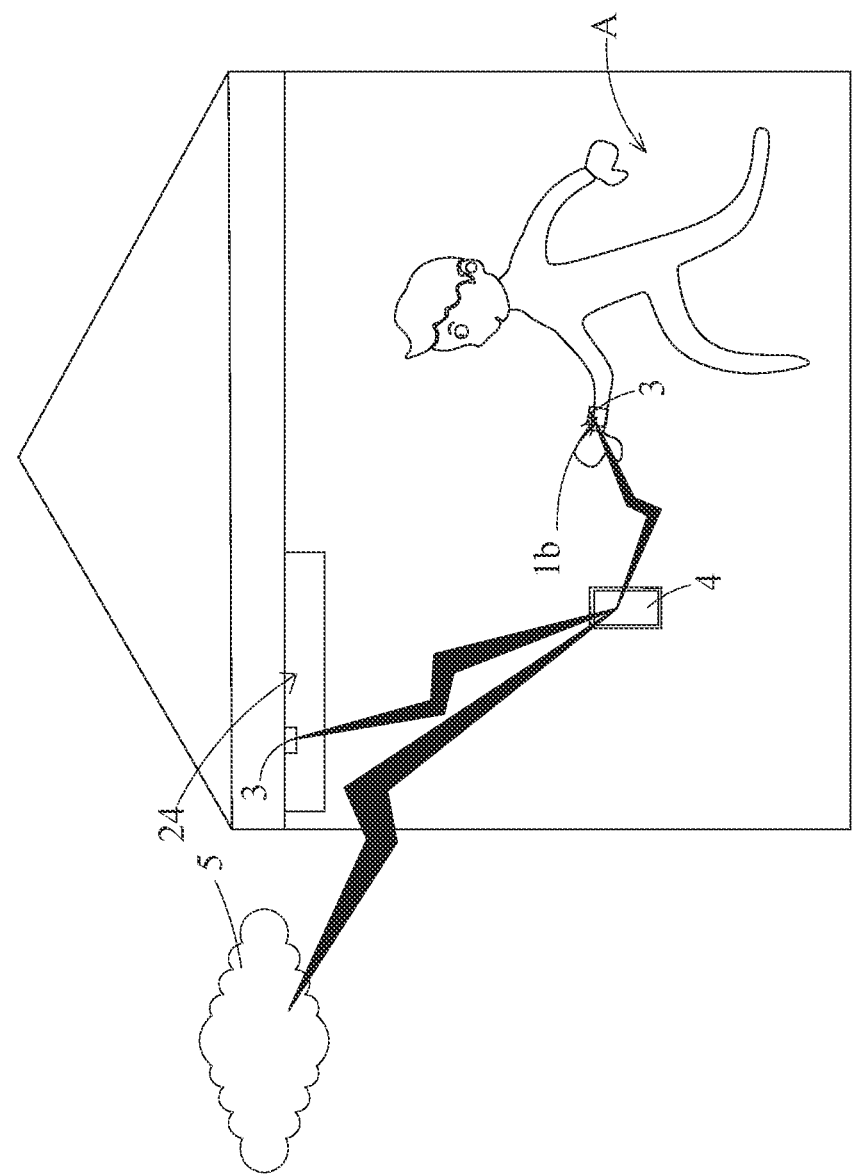
FIG. 1C illustrates a schematic view (2) for the operation of the method for preventing and handling indoor air pollution of the exemplary embodiment of the present disclosure.

Please refer to FIG. 1C. In one embodiment, the gas processing device is a cooker hood 24. The cooker hood 24 includes the gas detection module 3, and the microprocessor 33 of the gas detection module 3 is adapted to output a device gas detection data of the cooker hood to the communication device 34 to wirelessly transmit to the communication relay station 4, and the device gas detection data is further transmitted to the cloud processing device 5 for storage and intelligent computation and comparison. When the device gas detection data of the cooker hood 24 indicate that a location of the cooker hood 24 is in a polluted state, the cloud processing device 5 remotely transmits the control command to the communication relay station 4, and the control command is further transmitted to the gas detection module 3 of the cooker hood 24, so as to intelligently and selectively enable the cooker hood 24 and control an operation time of the cooker hood 24, so that the polluted gas at the location of the cooker hood 24 is discharged to the outdoor space in real-time, thereby allowing the indoor gas detection data of the polluted gas in the indoor space A to be decreased to the safety detection value.

Furthermore, when the cloud processing device 5 compares the indoor gas detection data with the outdoor gas detection data and determines that the indoor gas detection data is better than the outdoor gas detection data, and when the device gas detection data of the cooker hood 24 indicates that the location of the cooker hood 24 is in the polluted state, the cloud processing device 5 remotely transmits the control command to the communication relay station 4, and the control command is further transmitted to the gas detection module 3 of the gas exchanger 21 and the gas detection module 3 of the cooker hood 24, so as to intelligently and selectively disable the gas exchanger 21 so that the outdoor gas is not introduced into the indoor space A, and to intelligently and selectively enable the cooker hood 24 and control the operation time of the cooker hood 24 so that the polluted gas at the location of the cooker hood 24 is discharged to the outdoor space in real-time, thereby allowing the indoor gas detection data of the polluted gas in the indoor space A to be decreased to the safety detection value. The gas detection module 3 of the cooker hood 24 is adapted to output a reminder as an indication for replacing filtering consumables of the cooker hood 24.

Figure 1D:
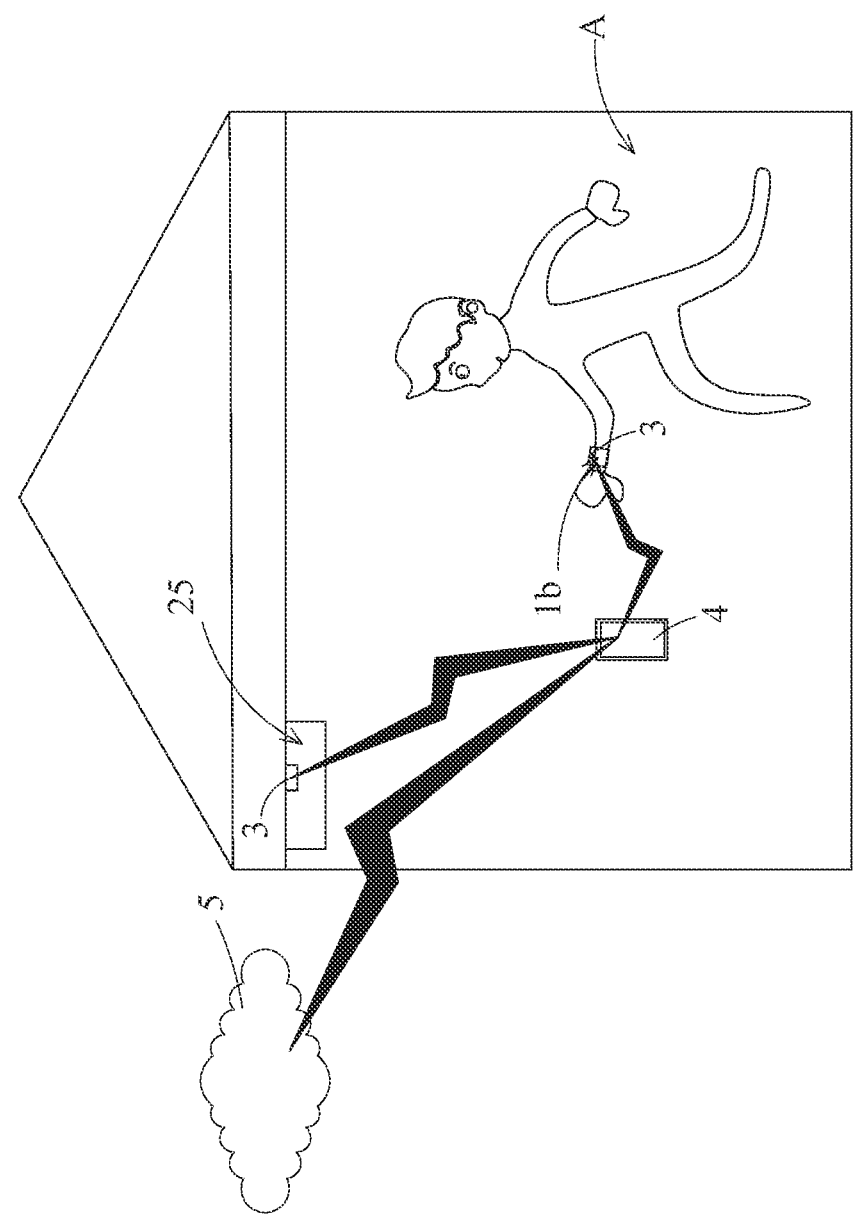
FIG. 1D illustrates a schematic view (3) for the operation of the method for preventing and handling indoor air pollution of the exemplary embodiment of the present disclosure.

Please refer to FIG. 1D. In one embodiment, the gas processing device is a ventilator 25. The ventilator 25 includes the gas detection module 3, and the microprocessor 33 of the gas detection module 3 is adapted to output a device gas detection data of the ventilator 25 to the communication device 34 to wirelessly transmit to the communication relay station 4, and the device gas detection data is further transmitted to the cloud processing device 5 for storage and intelligent computation and comparison. When the device gas detection data of the ventilator 25 indicates that a location of the ventilator 25 is in the polluted state, the cloud processing device 5 remotely transmits the control command to the communication relay station 4, and the control command is further transmitted to the gas detection module 3 of the ventilator 25 to intelligently and selectively enable the ventilator 25 and control an operation time of the ventilator 25, so that the polluted gas at the location of the ventilator 25 is discharged to the outdoor space in real-time, thereby allowing the indoor gas detection data of the polluted gas in the indoor space A to be decreased to the safety detection value.

Furthermore, when the cloud processing device 5 compares the indoor gas detection data with the outdoor gas detection data and determines that the indoor gas detection data is better than the outdoor gas detection data, and when the device gas detection data of the ventilator 25 indicates that the location of the ventilator 25 is in the polluted state, the cloud processing device 5 remotely transmits the control command to the communication relay station 4, and the control command is further transmitted to the gas detection module 3 of the gas exchanger 21 and the gas detection module 3 of the ventilator 25, so as to intelligently and selectively disable the gas exchanger 21 so that the outdoor gas is not introduced into the indoor space A, and to intelligently and selectively enable the ventilator 25 and control the operation time of the ventilator 25 so that the polluted gas at the location of the ventilator 25 is discharged to the outdoor space in real-time, thereby allowing the indoor gas detection data of the polluted gas in the indoor space A to be decreased to the safety detection value.

Please refer to FIG. 1E. In this embodiment, the gas processing device is an electric fan 26. The electric fan 26 includes the gas detection module 3, and the microprocessor 33 of the gas detection module 3 is adapted to output a device gas detection data of the electric fan 26 to the communication device 34 to wirelessly transmit to the communication relay station 4, and the device gas detection data is further transmitted to the cloud processing device 5 for storage and intelligent computation and comparison. When the device gas detection data of the electric fan 26 indicates that a location of the electric fan 26 is in a polluted state, the cloud processing device 5 remotely transmits the control command to the communication relay station 4, and the control command is further transmitted to the gas detection module 3 of the electric fan 26 to intelligently and selectively enable the electric fan 26 and control an operation time of the electric fan 26, and a convection of the polluted gas at the location of the electric fan 26 is accelerated in real-time, thereby allowing the indoor gas detection data of the polluted gas in the indoor space. A to be decreased to the safety detection value.

Furthermore, when the cloud processing device 5 compares the indoor gas detection data with the outdoor gas detection data and determines that the indoor gas detection data is better than the outdoor gas detection data, and when the device gas detection data of the electric fan 26 indicates that the location of the electric fan 26 is in the polluted state, the cloud processing device 5 remotely transmits the control command to the communication relay station 4, and the control command is further transmitted to the gas detection module 3 of the gas exchanger 21 and the gas detection module 3 of the electric fan 26, so as to intelligently and selectively disable the gas exchanger 21 so that the outdoor gas is not introduced into the indoor space A, and to intelligently and selectively enable the electric fan 26 and control the operation time of the electric fan 26, so as to accelerate the convection of the polluted gas at the location of the electric fan 26 in real-time, thereby allowing the indoor gas detection data of the polluted gas in the indoor space A to be decreased to the safety detection value.

The safety detection value includes at least one selected from the group consisting of a concentration of PM2.5 which is less than 10 $\mu g/m^3$, a concentration of carbon dioxide which is less than 1000 ppm, a concentration of total volatile organic compounds which is less than 0.56 ppm, a concentration of formaldehyde which is less than 0.08 ppm, a number of bacteria which is less than 1500 $CFU/m^3$, a number of fungi which is less than 1000 $CFU/m^3$, a concentration of sulfur dioxide which is less than 0.075 ppm, a concentration of nitrogen dioxide which is less than 0.1 ppm, a concentration of carbon monoxide which is less than 35 ppm, a concentration of ozone which is less than 0.12 ppm, and a concentration of lead which is less than 0.15 $\mu g/m^3$.

Moreover, the cleaning unit 213 of the gas exchanger 21 may be the combination of various embodiments. In one embodiment, the cleaning unit 23 may be a high-efficiency particulate air (HEPA) filter 213a. When the polluted gas is introduced into the inlet channel 212 from the gas inlet 211 by the flow-guiding component 214, the chemical smog, bacteria, dusts, particles, and pollens contained in the polluted gas are absorbed by the high-efficiency particulate air filter 213a, thereby the gas introduced into the gas exchanger 21 is filtered and purified. In some embodiments, a cleansing factor layer having chlorine dioxide is coated on the high-efficiency particulate air filter 213a for suppressing viruses, bacteria, fungus, influenza A virus, influenza B virus, Enterovirus, and Norovirus in the polluted gas introduced into the gas exchanger 21. Accordingly, the suppressing rate may exceed 99%, thereby allowing the reduction of the cross infections of the viruses. In some other embodiments, a herbal protection coating layer including the extracts of *Rhus chinensis* Mill (may be *Rhus chinensis* Mill from Japan) and the extracts of *Ginkgo biloba* may be coated on the high-efficiency particulate air filter 213a to form a herbal protection anti-allergy filter which can efficiently perform anti-allergy function and destroy cell surface proteins of influenza viruses (e.g., influenza virus subtype H1N1) passing through the herbal protection anti-allergy filter. Alternatively, in some other embodiments, a layer of silver ions may be coated on the high-efficiency particulate air filter 213a for suppressing viruses, bacteria, and fungus in the polluted gas introduced by the gas exchanger 21.

In another embodiment, the cleaning unit 213 may be a combination of the high-efficiency particulate air filter 213a and a photocatalyst unit 213b. The photocatalyst unit 213b includes a photocatalyst 2131b and an ultraviolet light 2132b. The photocatalyst 2131b is excited under the illumination of the ultraviolet light 2132b so as to degrade the pollutants in the polluted gas introduced by the gas exchanger 21 for filtering and purifying. The photocatalyst 2131b and the ultraviolet light 2132b are individually disposed in the inlet channel 212 and spaced apart from each other for a distance. When the gas exchanger 21 introduces the outdoor gas into the inlet channel 212 by the flow-guiding component 214, the photocatalyst 2131b is excited under the illumination of the ultraviolet light 2132b to convert the light energy into chemical energy, thereby degrading hazardous matters in the polluted gas and sterilizing the polluted gas, such that the polluted gas is filtered and purified by the cleaning unit 213.

In another embodiment, the cleaning unit 213 may be a combination of the high-efficiency particulate air filter 213a and a photo plasma unit 213c. The photo plasma unit 213c includes a nanometer light tube. Through illuminating the polluted gas introduced from the gas exchanger 21 with the light irradiated from the nanometer light tube, the volatile organic gases contained in the polluted gas can be degraded and purified. The nanometer light tube is disposed in the inlet channel 212. When the gas exchanger 21 introduces the outdoor gas into the inlet channel 212 by the flow-guiding component 214, the introduced polluted gas is illuminated by the light irradiated from the nanometer light tube, so that the oxygen molecules and water molecules in the polluted gas are degraded into high oxidative photo plasma, thereby forming a plasma stream capable of destroying organic molecules. Accordingly, volatile organic compounds (VOC) such as formaldehyde and toluene in the polluted gas can be degraded into water and carbon dioxide. Thus, the polluted gas can be filtered and purified by the cleaning unit 213.

In another embodiment, the cleaning unit 213 may be a combination of the high-efficiency particulate air filter 213a and a negative ion unit 213d. The negative ion unit 213d includes at least one electrode wire 2131d, at least one dust-collecting plate 2132d, and a boost power supply 2133d. Through high voltage discharging of the electrode wire 2131d, the particulates contained in the polluted gas introduced from the outdoor space by the gas exchanger 21 are adhered to the dust-collecting plate 2132d for being filtered and purified. The electrode wire 2131d and the dust-collecting plate 2132d are disposed in the inlet channel 212. The boost power supply 2133d provides the electrode wire 2131d with high voltage electricity, so as to allow the dust-collecting plate 2132d to carry with negative charges thereon. Therefore, when the gas exchanger 21 introduces the outdoor gas into the inlet channel 212 by the flow-guiding component 214, the electrode wire 2131d discharges electricity under a high voltage, so that particulates carry with positive charges in the polluted gas are adhered to the dust-collecting plate 2132d carry with negative charges. Accordingly, the polluted gas is filtered and purified by the cleaning unit 213.

In another embodiment, the cleaning unit 213 may be a combination of the high-efficiency particulate air filter 213a and a plasma ion unit 213e. The plasma ion unit 213e includes a first electric-field protection mesh 2131e, an absorbing mesh 2132e, a high-voltage discharge electrode 2133e, a second electric-field protection mesh 2134e, and a boost power supply 2135e. The boost power supply 2135e provides the high-voltage discharge electrode 2133e with a high voltage so as to generate a high-voltage plasma column. Therefore, the viruses and the bacteria in the polluted gas in the outdoor space introduced by the gas exchanger 21 are degraded by the high-voltage plasma column. The first electric-field protection mesh 2131e, the absorbing mesh 2132e, the high-voltage discharge electrode 2133e, and the second electric-field protection mesh 2134e are disposed in the inlet channel 212, and the absorbing mesh 2132e and the high-voltage discharge electrode 2133e are located between the first electric-field protection mesh 2131e and the second electric-field protection mesh 2134e. The high-voltage discharge electrode 2133e is provided with a high voltage by the boost power supply 2135e to generate a high-voltage plasma column. Therefore, when the outdoor gas is introduced into the inlet channel 212 by the flow-guiding component 214 of the gas exchanger 21, the oxygen molecules and the water molecules in the gas are ionized to form cations ($H^+$) and anions ($O_2^-$). The substances attached with water molecules around the ions are attached on the surfaces of viruses and bacteria, and converted the water molecules into oxidative oxygen ions (hydroxyl ions, $OH^-$ ions), and the oxidative oxygen ions take away the hydrogen ions of the proteins on the surfaces of the viruses and the bacteria to degrade the viruses and the bacteria. Accordingly, the polluted gas is filtered and purified by the cleaning unit 213.

In one embodiment, the cleaning unit 213 may only include the high-efficiency particulate air filter 213a. Alternatively, in another embodiment, the cleaning unit 213 may be a combination of the high-efficiency particulate air filter 213a and any one of the photocatalyst unit 213b, the photo plasma unit 213c, the negative ion unit 213d, and the plasma ion unit 213e. In one embodiment, the cleaning unit 213 may be a combination of the high-efficiency particulate air filter 213a and any two of the photocatalyst unit 213b, the photo plasma unit 213c, the negative ion unit 213d, and the plasma ion unit 213e. In one embodiment, the cleaning unit 213 may be a combination of the high-efficiency particulate air filter 213a and any three of the photocatalyst unit 213b, the photo plasma unit 213c, the negative ion unit 213d, and the plasma ion unit 213e. In one embodiment, the cleaning unit 213 may be a combination of the high-efficiency particulate air filter 213a and all of the photocatalyst unit 213b, the photo plasma unit 213c, the negative ion unit 213d, and the plasma ion unit 213e.

In one embodiment, the flow-guiding component 214 may be a fan, but not limited to a vortex fan or a centrifugal fan. Moreover, the enablement/disablement of the flow-guiding component 214 may be controlled by the gas detection module 3. Furthermore, the air volume of the flow-guiding component 214 may also be controlled by the control driving unit 219, and the air volume is in a range between 200 and 1600 of the clean air delivery rate (CADR).

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method for intelligently preventing and handling indoor air pollution by filtering and exchanging of a polluted gas in an indoor space, wherein the method comprises:
   detecting the polluted gas in an outdoor space and transmitting an outdoor gas detection data obtained therefrom, wherein an outdoor gas detector is provided to detect the polluted gas in the outdoor space and transmit the outdoor gas detection data of the outdoor space;
   detecting the polluted gas in the indoor space and transmitting an indoor gas detection data obtained therefrom, wherein an indoor gas detector is provided to detect the polluted gas in the indoor space and transmit the indoor gas detection data of the indoor space;
   providing an indoor gas exchange system in the indoor space for purification so as to detect and transmit a device gas detection data, wherein the indoor gas exchange system comprises at least one gas processing device conducting a purification of the polluted gas in the indoor space, the at least one gas processing device detects to obtain and transmits the device gas detection data of the polluted gas at a location of the at least one gas processing device; and
   providing a cloud processing device to receive and intelligently compare the outdoor gas detection data, the indoor gas detection data, and the device gas detection data with each other to intelligently and selectively control, the at least one gas processing device to conduct the purification by gas exchanging of the polluted gas in the indoor space to the outdoor space;
   wherein, a communication relay station is provided to receive and transmit the outdoor gas detection data, the indoor gas detection data, and the device gas detection data to the cloud processing device for storage and intelligent computation and comparison, wherein, in response to the comparison, the cloud processing device transmits a control command to the communication relay station, and the control command is further transmitted to the at least one gas processing device to intelligently and selectively enable the at least one gas processing device and control an operation time of the at least one gas processing device so as to exchange the polluted gas in the indoor space to the outdoor space and provide the purification of the polluted gas at the location of the at least one gas processing device to filter and purify , the polluted gas at a location of the at least one gas processing device in real-time to decrease, the indoor gas detection data of the polluted gas in the indoor space to a safety detection value, and to exchange the polluted gas in the indoor space into a clean, safe, and breathable gas.

2. The method for intelligently preventing and handling indoor air pollution according to claim 1, wherein the indoor gas detector is worn on a human body to detect the polluted gas in the indoor space in real-time.

3. The method for intelligently preventing and handling indoor air pollution according to claim 1, wherein the polluted gas comprises at least one selected from the group consisting of particulate matters, carbon monoxide, carbon dioxide, ozone, sulfur dioxide, nitrogen dioxide, lead, total volatile organic compounds, formaldehyde, bacteria, fungi, and viruses.

4. The method for intelligently preventing and handling indoor air pollution according to claim 1, wherein each of the outdoor gas detector, the indoor gas detector, and the at least one gas processing device independently comprises a gas detection module.

5. The method for intelligently preventing and handling indoor air pollution according to claim 4, wherein the gas detection module comprises a control circuit board, a gas detection main body, a microprocessor, and a communication device; wherein the gas detection main body, the microprocessor, and the communication device are integrally packaged with and electrically connected to the control circuit board; the microprocessor controls the detection of the gas detection main body and the detection signal generated from the detection of the polluted gas is received and processed by the microprocessor; and wherein the microprocessor in the outdoor gas detector, the microprocessor in the indoor gas detector, and the microprocessor in the at least one gas processing device output the outdoor gas detection data, the indoor gas detection data, and the device gas detection data, respectively, to the communication devices for wirelessly transmitting outwardly.

6. The method for intelligently preventing and handling indoor air pollution according to claim 5, wherein the gas detection main body comprises:
   a base, having:
   a first surface;
   a second surface opposite to the first surface;
   a laser configuration region hollowed out from the first surface to the second surface;
   a gas inlet groove recessed from the second surface and located adjacent to the laser configuration region, wherein the gas inlet groove has a gas inlet through hole and two lateral walls; two light permissive windows penetrate on the two lateral walls of the gas inlet groove and in communication with the laser configuration region;
   a gas-guiding component loading region recessed from the second surface and in communication with the gas inlet groove, wherein a gas flowing hole penetrates a bottom surface of the gas-guiding component loading region; and
   a gas outlet groove includes a first region, corresponding to the gas-guiding component loading region, recessed from a portion of the first surface corresponding to the bottom surface of the gas-guiding component loading region; and a second region, not corresponding to the gas-guiding component loading region, hollowed out from the first surface to the second surface in a region where the first surface, wherein the gas outlet groove is in communication with the gas flowing hole and has a gas outlet through hole;

a piezoelectric actuator received in the gas-guiding component loading region to allow the polluted gas to be introduced in the gas inlet groove;

a driving circuit board attached to the second surface of the base;

a laser component disposed on and electrically connected to the driving circuit board, wherein the laser component is received in the laser configuration region, and a path of a light beam emitted by the laser component passes through the light permissive windows and is orthogonal to the gas inlet groove;

a particulate sensor disposed on and electrically connected to the driving circuit board, wherein the particulate sensor is received in a portion of the gas inlet groove where the path of the light beam emitted by the laser component is orthogonal thereto, so that the particulate sensor detects particulates in the polluted gas passing through the gas inlet groove which is illuminated by the light beam of the laser component;

a gas sensor disposed on and electrically connected to the driving circuit board, wherein the gas sensor is received in the gas outlet groove, so that the gas sensor detects the polluted gas introduced into the gas outlet groove; and an outer cap covering the base and having a side plate, and the side plate has a gas inlet opening and a gas outlet opening, the gas inlet opening is corresponding to the gas inlet through hole of the base, and the gas outlet opening is corresponding to the gas outlet through hole of the base;

wherein the outer cap is covered on the base, and the driving circuit board is attached to the second surface of the base, so that the gas inlet groove defines a gas inlet path and the gas outlet groove defines a gas outlet path, to facilitate the piezoelectric actuator to introduce the polluted gas outside the gas inlet through hole of the base into the gas inlet path defined by the gas inlet groove from the gas inlet opening;

the polluted gas passes through the particulate sensor to be detected to obtain a particle concentration of the particulates in the polluted gas; and the polluted gas is discharged into the gas outlet path defined by the gas outlet groove from the gas flowing hole, detected by the gas sensor, and is discharged out of the gas detection main body from the gas outlet through hole and the gas outlet opening of the base.

7. The method for intelligently preventing and handling indoor air pollution according to claim 6, wherein the particulate sensor detects particulate matters.

8. The method for intelligently preventing and handling indoor air pollution according to claim 6, wherein the gas sensor comprises at least one selected from the group consisting of a volatile organic compound detector, a formaldehyde sensor, a bacterial sensor, and a virus sensor; the volatile organic compound detector detects carbon dioxide or total volatile organic compounds; the formaldehyde sensor detects formaldehyde (HCHO) gas; the bacterial sensor detects bacteria or fungi; the virus sensor is capable of detecting viruses.

9. The method for intelligently preventing and handling indoor air pollution according to claim 5, wherein the at least one gas processing device is a gas exchanger for guiding an outdoor gas of the outdoor space into the indoor space for gas exchange; the gas exchanger comprises at least one gas inlet, an inlet channel, a cleaning unit, at least one flow-guiding component, at least one gas outlet, at least one gas-exchange inlet, a gas-exchange channel, and at least one gas-exchange outlet, and the gas exchanger comprises the gas detection module to enable the flow-guiding component; the at least one gas inlet is connected to the inlet channel; the cleaning unit is disposed in the inlet channel; the at least one gas outlet is in communication with the inlet channel and connected to the at least one flow-guiding component; and the at least one gas-exchange inlet is connected to the gas-exchange channel which is in communication with the at least one gas-exchange outlet; the microprocessor of the gas detection module outputs the gas device detection data to the communication device for wirelessly transmission outwardly; the communication device of the gas detection module receives the control command transmitted by the communication relay station to intelligently control the introduction of the outdoor gas into the indoor space, so that the polluted gas in the indoor space is exchanged with the outdoor gas, to decrease the indoor gas detection data of the polluted gas in the indoor space to the safety detection value.

10. The method for intelligently preventing and handling indoor air pollution according to claim 9, wherein when the cloud processing device compares the indoor gas detection data with the outdoor gas detection data and determines that the outdoor gas detection data is better than the indoor gas detection data, the cloud processing device remotely transmits the control command to the communication relay station, and the control command is further transmitted to the gas detection module to intelligently and selectively enable the gas exchanger and control an operation time of the gas exchanger, so that the flow-guiding component is enabled to introduce the outdoor gas into the inlet channel from the at least one gas inlet, pass through the cleaning unit for filtering and purifying, and into the at least one gas outlet to enter into the indoor space, and the polluted gas in the indoor space is introduced into the gas-exchange channel from the at least one gas-exchange inlet and discharged to the outdoor space from the at least one gas-exchange outlet, to exchange the polluted gas in the indoor space to the outdoor space and to purify the polluted gas at the location of the gas exchanger in real-time, so that the indoor gas detection data of the polluted gas in the indoor space is decreased to the safety detection value.

11. The method for intelligently preventing and handling indoor air pollution according to claim 9, wherein when the cloud processing device compares the indoor gas detection data with the outdoor gas detection data and determines that the indoor gas detection data is better than the outdoor gas detection data, the cloud processing device remotely transmits the control command to the communication relay station, and the control command is further transmitted to the gas detection module of the gas exchanger to intelligently and selectively disable the gas exchanger, so that the outdoor gas is not introduced into the indoor space, to decrease the indoor gas detection data of the polluted gas in the indoor space to the safety detection value.

12. The method for intelligently preventing and handling indoor air pollution according to claim 9, wherein the cleaning unit is a high-efficiency particulate air filter.

13. The method for intelligently preventing and handling indoor air pollution according to claim 12, wherein the high-efficiency particulate air filter is coated with at least one selected from the group consisting of a cleansing factor layer having chlorine dioxide, a herbal protection coating layer including extracts of *Rhus chinensis* Mill and extracts of Ginkgo biloba, and a layer of silver ions to suppress viruses and bacteria in the polluted gas.

14. The method for intelligently preventing and handling indoor air pollution according to claim 12, wherein the cleaning unit further comprises at least one selected from the group consisting of a photocatalyst unit, a photo plasma unit, a negative ion unit, and a plasma ion unit.

15. The method for intelligently preventing and handling indoor air pollution according to claim 9, wherein the cloud processing device further comprises a gas molding flow simulation system adapted to calculate a number of the gas exchanger installed in the indoor space, a gas flow field direction of the indoor space, and locations of gas pipelines, gas entrances and gas exits for installing the gas exchanger.

16. The method for intelligently preventing and handling indoor air pollution according to claim 5, wherein the at least one gas processing device is a cleaner;
the cleaner comprises the gas detection module, and the microprocessor of the gas detection module in the cleaner is adapted to output the device gas detection data of the cleaner to the communication device to wirelessly transmit the device gas detection data of the cleaner to the communication relay station, and the device gas detection data of the cleaner is further transmitted to the cloud processing device for storage and intelligent computation and comparison;
when the device gas detection data of the cleaner indicates that a location of the cleaner is in a polluted state, the cloud processing device remotely transmits the control command to the communication relay station, and the control command is further transmitted to the gas detection module of the cleaner, so that the gas detection module in the cleaner intelligently and selectively enables the cleaner and controls an operation time of the cleaner, to filter and purify the polluted gas at the location of the cleaner in real-time so as to decrease the indoor gas detection data of the polluted gas in the indoor space to the safety detection value.

17. The method for intelligently preventing and handling indoor air pollution according to claim 16, wherein when the cloud processing device compares the indoor gas detection data with the outdoor gas detection data and determines that the indoor gas detection data is better than the outdoor gas detection data, and when the device gas detection data of the cleaner indicates that the location of the cleaner is in the polluted state, the cloud processing device remotely transmits the control command to the communication relay station, and the control command is further transmitted to the gas detection module of the gas exchanger and the gas detection module of the cleaner,
so as to intelligently an selectively disable the gas exchanger so that the outdoor gas is not introduced into the indoor space, and to intelligently and selectively enable the cleaner and control the operation time of the cleaner to filter and purify the polluted gas at the location of the cleaner in real-time, so as to decrease the indoor gas detection data of the polluted gas in the indoor space to the safety detection value.

18. The method for intelligently preventing and handling indoor air pollution according to claim 17, the gas detection module of the cleaner is adapted to output a reminder as an indication for replacing filtering consumables of the cleaner.

19. The method for intelligently preventing and handling indoor air pollution according to claim 5, wherein the at least one gas processing device is an air conditioner; the air conditioner comprises the gas detection module, and the microprocessor of the gas detection module in the air conditioner is adapted to output the device gas detection data of the air conditioner to the communication device to wirelessly transmit to the communication relay station, and the device gas detection data of the air conditioner is further transmitted to the cloud processing device for storage and intelligent computation and comparison;
when the device gas detection data of the air conditioner indicates that a location of the air conditioner is in a polluted state, the cloud processing device remotely transmits the control command to the communication relay station, and the control command is further transmitted to the gas detection module of the air conditioner to intelligently and selectively enable the air conditioner and control an operation time of the air conditioner, so as to filter and purify the polluted gas at the location of the air conditioner in real-time and adjust a temperature, a humidity, and a gas flow in the indoor space, and thus to decrease the indoor gas detection data of the polluted gas in the indoor space to the safety detection value.

20. The method for intelligently preventing and handling indoor air pollution according to claim 19, wherein when the cloud processing device compares the indoor gas detection data with the outdoor gas detection data and determines that the indoor gas detection data is better than the outdoor gas detection data, and when the device gas detection data of the air conditioner indicates that the location of the air conditioner is in the polluted state, the cloud processing device remotely transmits the control command to the communication relay station, and the control command is further transmitted to the gas detection module of the gas exchanger and the gas detection module of the air conditioner,
so as to intelligently and selectively disable the gas exchanger so that the outdoor gas is not introduced into the indoor space, and to intelligently and selectively enable the air conditioner and control the operation time of the air conditioner to filter and purify the polluted gas at the location of the air conditioner in real-time and adjust the temperature, the humidity, and the gas flow in the indoor space, and thus to decrease the indoor gas detection data of the polluted gas in the indoor space to the safety detection value.

21. The method for intelligently preventing and handling indoor air pollution according to claim 20, the gas detection module of the air conditioner is adapted to output a reminder as an indication for replacing filtering consumables of the air conditioner.

22. The method for intelligently preventing and handling indoor air pollution according to claim 5, wherein the at least one gas processing device is a cooker hood; the cooker hood comprises the gas detection module, and the microprocessor of the gas detection module in the cooker hood is adapted to output the device gas detection data of the cooker hood to the communication device to wirelessly transmit to the communication relay station, and the device gas detection data of the cooker hood is further transmitted to the cloud processing device for storage and intelligent computation and comparison;
when the device gas detection data of the cooker hood indicates that a location of the cooker hood is in a polluted state, the cloud processing device remotely transmits the control command to the communication relay station, and the control command is further transmitted to the gas detection module of the cooker hood to intelligently and selectively enable the cooker hood and control an operation time of the cooker hood to discharge the polluted gas at the location of the cooker hood to the outdoor space in real-time, so as to decrease the indoor gas detection data of the polluted gas in the indoor space to the safety detection value.

23. The method for intelligently preventing and handling indoor air pollution according to claim 22, wherein when the cloud processing device compares the indoor gas detection data with the outdoor gas detection data and determines that the indoor gas detection data is better than the outdoor gas detection data, and when the device gas detection data of the cooker hood indicates that the location of the cooker hood is in the polluted state, the cloud processing device remotely transmits the control command to the communication relay station, and the control command is further transmitted to the gas detection module of the gas exchanger and the gas detection module of the cooker hood,
so as to intelligently and selectively disable the gas exchanger so that the outdoor gas is not introduced into the indoor space, and to intelligently and selectively enable the cooker hood and control the operation time of the cooker hood to discharge the polluted gas at the location of the cooker hood to the outdoor space in real-time, so as to decrease the indoor gas detection data of the polluted gas in the indoor space to the safety detection value.

24. The method for intelligently preventing and handling indoor air pollution according to claim 23, the gas detection module of the cooker hood is adapted to output a reminder as an indication for replacing filtering consumables of the cooker hood.

25. The method for intelligently preventing and handling indoor air pollution according to claim 5, wherein the at least one gas processing device is a ventilator;
the ventilator comprises the gas detection module, and the microprocessor of the gas detection module in the ventilator is adapted to output the device gas detection data of the ventilator to the communication device to wirelessly transmit to the communication relay station, and the device gas detection data of the ventilator is further transmitted to the cloud processing device for storage and intelligent computation and comparison;
when the device gas detection data of the ventilator indicates that a location of the ventilator is in a polluted state, the cloud processing device remotely transmits the control command to the communication relay station, and the control command is further transmitted to the gas detection module of the ventilator, so as to intelligently and selectively enable the ventilator and control an operation time of the ventilator to discharge, the polluted gas at the location of the ventilator to the outdoor space in real-time, so as to decrease the indoor gas detection data of the polluted gas in the indoor space to the safety detection value.

26. The method for intelligently preventing and handling indoor air pollution according to claim 25, wherein when the cloud processing device compares the indoor gas detection data with the outdoor gas detection data and determines that the indoor gas detection data is better than the outdoor gas detection data, and when the device gas detection data of the ventilator indicates that the location of the ventilator is in the polluted state, the cloud processing device remotely transmits the control command to the communication relay station, and the control command is further transmitted to the gas detection module of the gas exchanger and the gas detection module of the ventilator,
so as to intelligently and selectively disable the gas exchanger so that the outdoor gas is not introduced into the indoor space, and to intelligently and selectively enable the ventilator and control the operation time of the ventilator to discharge the polluted gas at the location of the ventilator to the outdoor space in real-time, so as to decrease the indoor gas detection data of the polluted gas in the indoor space to the safety detection value.

27. The method for intelligently preventing and handling indoor air pollution according to claim 9, wherein the at least one gas processing device is a an electric fan; the electric fan comprises the gas detection module, and the microprocessor of the gas detection module in the electric fan is adapted to output the device gas detection data of the electric fan to the communication device to wirelessly transmit to the communication relay station, and the device gas detection data of the electric fan is further transmitted to the cloud processing device for storage and intelligent computation and comparison;
when the device gas detection data of the electric fan indicates that a location of the electric fan is in a polluted state, the cloud processing device remotely transmits the control command to the communication relay station, and the control command is further transmitted to the gas detection module of the electric fan to intelligently and selectively enable the electric fan and control an operation time of the electric fan, so as to accelerate a convection of the polluted gas at the location of the electric fan in real-time, and thus to decrease the indoor gas detection data of the polluted gas in the indoor space to the safety detection value.

28. The method for intelligently preventing and handling indoor air pollution according to claim 27, wherein when the cloud processing device compares the indoor gas detection data with the outdoor gas detection data and determines that the indoor gas detection data is better than the outdoor gas detection data, and when the device gas detection data of the electric fan indicates that the location of the electric fan is in the polluted state, the cloud processing device remotely transmits the control command to the communication relay station, and the control command is further transmitted to the gas detection module of the gas exchanger and the gas detection module of the electric fan,
so as to intelligently and selectively disable the gas exchanger so that the outdoor gas is not introduced into the indoor space, and to intelligently and selectively enable the electric fan and control the operation time of the electric fan to accelerate the convection of the polluted gas at the location of the electric fan in real-time, so as to decrease the indoor gas detection data of the polluted gas in the indoor space to be decreased to the safety detection value.

29. The method for intelligently preventing and handling indoor air pollution according to claim 5, wherein the communication device is at least one selected from the group consisting of a Wi-Fi module, a Bluetooth module, a radiofrequency identification module, and a near field communication module.

30. The method for intelligently preventing and handling indoor air pollution according to claim 1, wherein the communication relay station transmits and receives the outdoor gas detection data, the indoor gas detection data, and the device gas detection data through a wireless transmission manner.

31. The method for intelligently preventing and handling indoor air pollution according to claim 30, wherein the wireless transmission manner is a Bluetooth transmission and the communication relay station is a mobile device, or the wireless transmission manner is a Wi-Fi transmission and the communication relay station is a router device.

32. The method for intelligently preventing and handling indoor air pollution according to claim 31, wherein the mobile device is adapted to display the outdoor gas detection data, the indoor gas detection data, and the device gas detection data so as to provide a notification in regards to a pollution condition in the indoor space and a precaution of the polluted gas.

33. The method for intelligently preventing and handling indoor air pollution according to claim 1, wherein the safety detection value comprises at least one selected from the group consisting of a concentration of particulate matter (PM2.5) which is less than 10 $g/m^3$, a concentration of carbon dioxide which is less than 1000 ppm, a concentration of total volatile organic compounds which is less than 0.56 ppm, a concentration of formaldehyde which is less than 0.08 ppm, a number of bacteria which is less than 1500 $CFU/m^3$, a number of fungi which is less than 1000 $CFU/m^3$, a concentration of sulfur dioxide which is less than 0.075 ppm, a concentration of nitrogen dioxide which is less than 0.1 ppm, a concentration of carbon monoxide which is less than 35 ppm, a concentration of ozone which is less than 0.12 ppm, and a concentration of lead which is less than 0.15 $g/m^3$.

* * * * *